(12) United States Patent
Brandstadt et al.

(10) Patent No.: US 7,455,998 B2
(45) Date of Patent: Nov. 25, 2008

(54) METHODS FOR FORMING STRUCTURALLY DEFINED ORGANIC MOLECULES

(75) Inventors: Kurt Friedrich Brandstadt, Frankenmuth, MI (US); Thomas Howard Lane, Midland, MI (US); John C. Saam, Midland, MI (US); Joseph C. McAuliffe, Sunnyvale, CA (US)

(73) Assignees: Dow Corning Corporation, Midland, MI (US); Genencor International, Inc., Palo Alto, CA (US)

( * ) Notice: Subject to any disclaimer, the term of this patent is extended or adjusted under 35 U.S.C. 154(b) by 480 days.

(21) Appl. No.: 10/791,951

(22) Filed: Mar. 3, 2004

(65) Prior Publication Data

US 2005/0196849 A1 Sep. 8, 2005

(51) Int. Cl.
*C12P 9/00* (2006.01)
*C12N 9/76* (2006.01)
*C12N 9/20* (2006.01)
*C12N 9/14* (2006.01)

(52) U.S. Cl. .................. 435/131; 435/213; 435/198; 435/195

(58) Field of Classification Search .......... None
See application file for complete search history.

(56) References Cited

U.S. PATENT DOCUMENTS

| 6,617,411 B1 | 9/2003 | Friedrich |
| 2003/0119156 A1* | 6/2003 | Sakkab .................. 435/131 |

| 2004/0077816 A1 | 4/2004 | Brandstadt et al. |

FOREIGN PATENT DOCUMENTS

| CA | 2422600 | * | 3/2002 |
| WO | WO 90/09446 A | | 8/1990 |
| WO | WO 02/22842 A1 | | 3/2002 |
| WO | WO 03/054205 A2 | | 7/2003 |

OTHER PUBLICATIONS

J.N. Cha et al. "Silicatein Filaments and Subunits From a Marine Sponge Direct the Polymerization of Silica and Silcones In vitro", PNAS 96: 361-365. (Jan. 1999).*
1997 Sigma Catalog, pp. 652-653.*
Bassindale et al., Enzyme-catalysed siloxane bond formation, Journal of Inorganic Biochemistry, May 21, 2003, pp. 401-406, Elsevier Inc.
Fattaklhova et al., Fermentative Hydrolysis of the Silicon-Oxygen Bond, Access Russia, Inc. pp. 100-105.
Nishino et al., Enzymatic silicon oligomerization catalyzed by a lipid-coated lipase, The Royal Society of Chemistry 2002, pp. 2684-2685.
Bassindale et al., Biocatalysis of Siloxane Bonds, Polymer Preprints 2003, 44(2), pp. 570-571.
Bassindale et al: "Siloxane Biocatalysis. Polymer Preprints." Mid-Mar. 2004, vol. 45, No. 1, pp. 614-615, see Scheme 3, p. 614.
Jamison et al: "Bridged Polygermsesquioxanes. Organically Modified Germanium Oxide Materials". Chemical Materials. Sep. 1993, vol. 5, No. 9, pp. 1193-1195, see p. 1194, left column.
Bassindale et al: "Enzyme-Catalyzed Siloxane Bond Formation". Journal Inorg. Chem. 2003, vol. 93, pp. 401-406, see Table 1, p. 405.

* cited by examiner

*Primary Examiner*—Rebecca E. Prouty
(74) *Attorney, Agent, or Firm*—Dinsmore & Shohl LLP

(57) ABSTRACT

Methods of forming organic molecules comprising contacting a hydrolase enzyme with an organic reactant are provided. Methods for forming an organosilicon molecule comprising contacting a hydrolase enzyme with an organosilicon reactant are also provided.

13 Claims, 25 Drawing Sheets

Figure 1 (SEQ ID NO:1)

SEQUENCE LISTING

<160> NUMBER OF SEQ ID NOS: 1

<210> SEQ ID NO 1
<211> LENGTH: 229
<212> TYPE: PRT
<213> ORGANISM: Artificial Sequence
<220> FEATURE:
<223> OTHER INFORMATION: Trypsinogen

<400> SEQUENCE: 1

```
Val Asp Asp Asp Asp Lys Ile Val Gly Gly Tyr Thr Cys Gly Ala Asn
1               5                   10                  15

Thr Val Pro Tyr Gln Val Ser Leu Asn Ser Gly Tyr His Phe Cys Gly
            20                  25                  30

Gly Ser Leu Ile Asn Ser Gln Trp Val Val Ser Ala Ala His Cys Tyr
                35                  40                  45

Lys Ser Gly Ile Gln Val Arg Leu Gly Asn Asp Asn Ile Asn Val Val
            50                  55                  60

Glu Gly Asn Gln Gln Phe Ile Ser Ala Ser Lys Ser Ile Val His Pro
65                  70                  75                  80

Ser Tyr Asn Ser Asn Thr Leu Asn Asn Asp Ile Met Leu Ile Lys Leu
                85                  90                  95

Lys Ser Ala Ala Ser Leu Asn Ser Arg Val Ala Ser Ile Ser Leu Pro
            100                 105                 110

Thr Ser Cys Ala Pro Ala Gly Thr Gln Cys Leu Ile Ser Gly Trp Gly
            115                 120                 125

Asn Thr Lys Ser Ser Gly Thr Ser Tyr Pro Asp Val Leu Lys Cys Leu
130                 135                 140

Lys Ala Pro Ile Leu Ser Asn Ser Ser Cys Lys Ser Ala Tyr Pro Gly
145                 150                 155                 160

Gln Ile Thr Ser Asn Met Phe Cys Ala Gly Tyr Leu Glu Gly Gly Lys
                165                 170                 175

Asp Ser Cys Gln Gly Asp Ser Gly Gly Pro Val Val Cys Ser Gly Lys
            180                 185                 190

Leu Gln Gly Ile Val Ser Trp Gly Ser Gly Cys Ala Gln Lys Asn Lys
            195                 200                 205

Pro Gly Val Tyr Thr Lys Val Cys Asn Tyr Val Ser Trp Ile Lys Gln
210                 215                 220

Thr Ile Ala Ser Asn
225
```

METHODS FOR FORMING STRUCTURALLY DEFINED ORGANIC MOLECULES

FIELD OF THE INVENTION

The present invention relates to methods for forming organic molecules, and more particularly, to methods for forming organic molecules comprising contacting a hydrolase enzyme with an organic reactant.

BACKGROUND OF THE INVENTION

The biomolecular mechanisms of numerous organic molecules are essentially undefined. Particularly, the organic molecules containing silicon are essential for growth and biological function in a variety of plant, animal, and microbial systems, however the molecular mechanism for these interactions are effectively unknown. The in vitro studies of natural systems within the area of silica biosynthesis are complicated. Early mechanistic queries including biomimetic approaches often failed to recognize the chemistry of silicic acid and its analogues. For example, silicatein was determined to catalyze the polycondensation of tetraethoxysilane during the formation of particulate silica. However, given the limitations of the product and the resultant analysis, the study was not able to differentiate between the role of silicatein in the hydrolysis and condensation reactions during biosilicification.

Thus, there remains a need for improved methods of forming structurally defined organic molecules and materials, particularly organosilicon molecules.

SUMMARY OF THE INVENTION

Accordingly, the present invention is directed to methods of forming an organic molecule. The method comprises contacting a hydrolase enzyme with an organic reactant. The organic reactant comprises the formula:

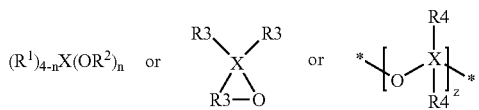

wherein X is selected from the group consisting of silicon and germanium; $R^1$ is selected from the group consisting of alkyl, haloalkyl, unsaturated alkyl, aryl, alcohol, epoxy, ether, amine, —$(OXR^4{}_2)_y$—$OXR^4{}_3$ and a combination thereof; $R^2$ is selected from the group consisting of alkyl, hydrogen, ether and a combination thereof; $R^3$ is selected from the group consisting of alkyl, unsaturated alkyl, aryl, hydrogen and a combination thereof; $R^4$ is selected from the group consisting of alkyl, haloalkyl, unsaturated alkyl, aryl, hydrogen, hydroxy, alkoxy, alcohol, epoxy, ether, amine, —$(OXR^4{}_2)_y$—$OXR^4{}_3$ and a combination thereof; n is an integer from 0 to 4; y is 0 or is an integer greater than 0; and z is 3 or an integer greater than 3. The hydrolase enzyme comprises lipase, protease, phosphoesterase, esterase, cutinase or a combination thereof. The hydrolase enzyme catalyzes the hydrolysis and condensation of the organic reactant to form the organic molecule.

In another embodiment of the invention, a method of forming an organosilicon molecule is provided. The method comprises contacting a hydrolase enzyme with an organosilicon reactant. The organosilicon reactant comprises the formula:

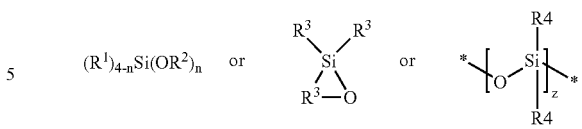

wherein: $R^1$ is selected from the group consisting of alkyl, haloalkyl, unsaturated alkyl, aryl, alcohol, epoxy, ether, amine, —$(OSiR^4{}_2)_y$—$OSiR^4{}_3$, and a combination thereof; $R^2$ is selected from the group consisting of alkyl, hydrogen, ether and a combination thereof; $R^3$ is selected from the group consisting of alkyl, unsaturated alkyl, aryl, hydrogen and a combination thereof; $R^4$ is selected from the group consisting of alkyl, haloalkyl, unsaturated alkyl, aryl, hydrogen, hydroxy, alkoxy, alcohol, epoxy, ether, amine, —$(OSiR^4{}_2)_y$—$OSiR^4{}_3$ and a combination thereof; n is an integer from 0 to 4; y is 0 or an integer greater than 0; and z is 3 or is an integer greater than 3. The hydrolase enzyme comprises lipase, protease, phosphoesterase, esterase, cutinase or a combination thereof. The hydrolase enzyme catalyzes the hydrolysis and condensation of the organosilicon reactant to form the organosilicon molecule.

In yet another embodiment of the present invention, a method of forming an organosilicon intermediate molecule is provided. The method comprises contacting a hydrolase enzyme with an organosilicon reactant. The organosilicon reactant comprises the formula:

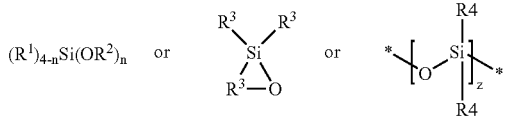

wherein: $R^1$ is selected from the group consisting of alkyl, haloalkyl, unsaturated alkyl, aryl, alcohol, epoxy, ether, amine, —$(OSiR^4{}_2)_y$—$OSiR^4{}_3$, and a combination thereof; $R^2$ is selected from the group consisting of alkyl, hydrogen, ether and a combination thereof; $R^3$ is selected from the group consisting of alkyl, unsaturated alkyl, aryl, hydrogen and a combination thereof; $R^4$ is selected from the group consisting of alkyl, haloalkyl, unsaturated alkyl, aryl, hydrogen, hydroxy, alkoxy, alcohol, epoxy, ether, amine, —$(OSiR^4{}_2)_y$—$OSiR^4{}_3$ and a combination thereof; n is an integer from 0 to 4; y is 0 or is an integer greater than 0; and z is 3 or is an integer greater than 3. The hydrolase enzyme comprises lipase, protease, phosphoesterase, esterase, cutinase or a combination thereof. The hydrolase enzyme catalyzes the hydrolysis of the organosilicon reactant to form the organosilicon intermediate molecule.

In yet another embodiment of the present invention a method of forming an organosilicon molecule is provided. The method comprises contacting a hydrolase enzyme with an organosilicon intermediate reactant. The organosilicon intermediate reactant comprises the formula:

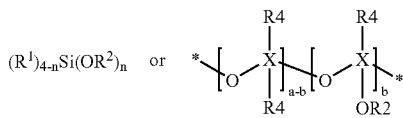

wherein $R^1$ is selected from the group consisting of alkyl, haloalkyl, unsaturated alkyl, aryl, alcohol, epoxy, ether, amine, —$(OSiR^4_2)_y$—$OSiR^4_3$, and combination thereof; $R^2$ is a hydrogen; $R^4$ is selected from the group consisting of alkyl, haloalkyl, unsaturated alkyl, aryl, hydrogen, hydroxy, alkoxy, alcohol, epoxy, ether, amine, —$(OSiR^4_2)_y$—$OSiR^4_3$ and a combination thereof; n is an integer from 0 to 4; and y is 0 or is an integer greater than 0; a+b equals z; and z is 3 or is an integer greater than 3. The hydrolase enzyme comprises lipase, protease, phosphoesterase, esterase, cutinase or a combination thereof. The hydrolase enzyme catalyzes the condensation of the organosilicon intermediate reactant to form the organosilicon molecule.

The ability to synthesize organic molecules under the presently defined reaction conditions is advantageous because the reaction conditions assist in hydrolysis and condensation of the organic reactant to form the organic molecule. Other advantages of the present invention will become apparent to those skilled in the art from the following detailed description where alternative exemplary embodiments of this invention are shown and described. As will be realized, the invention is capable of other different, obvious aspects and embodiments, all without departing from the invention. Accordingly, the drawing and descriptions should be regarded as illustrative in nature and not as restrictive.

DETAILED DESCRIPTION OF THE FIGURES

DETAILED DESCRIPTION OF THE INVENTION

Figure 1:
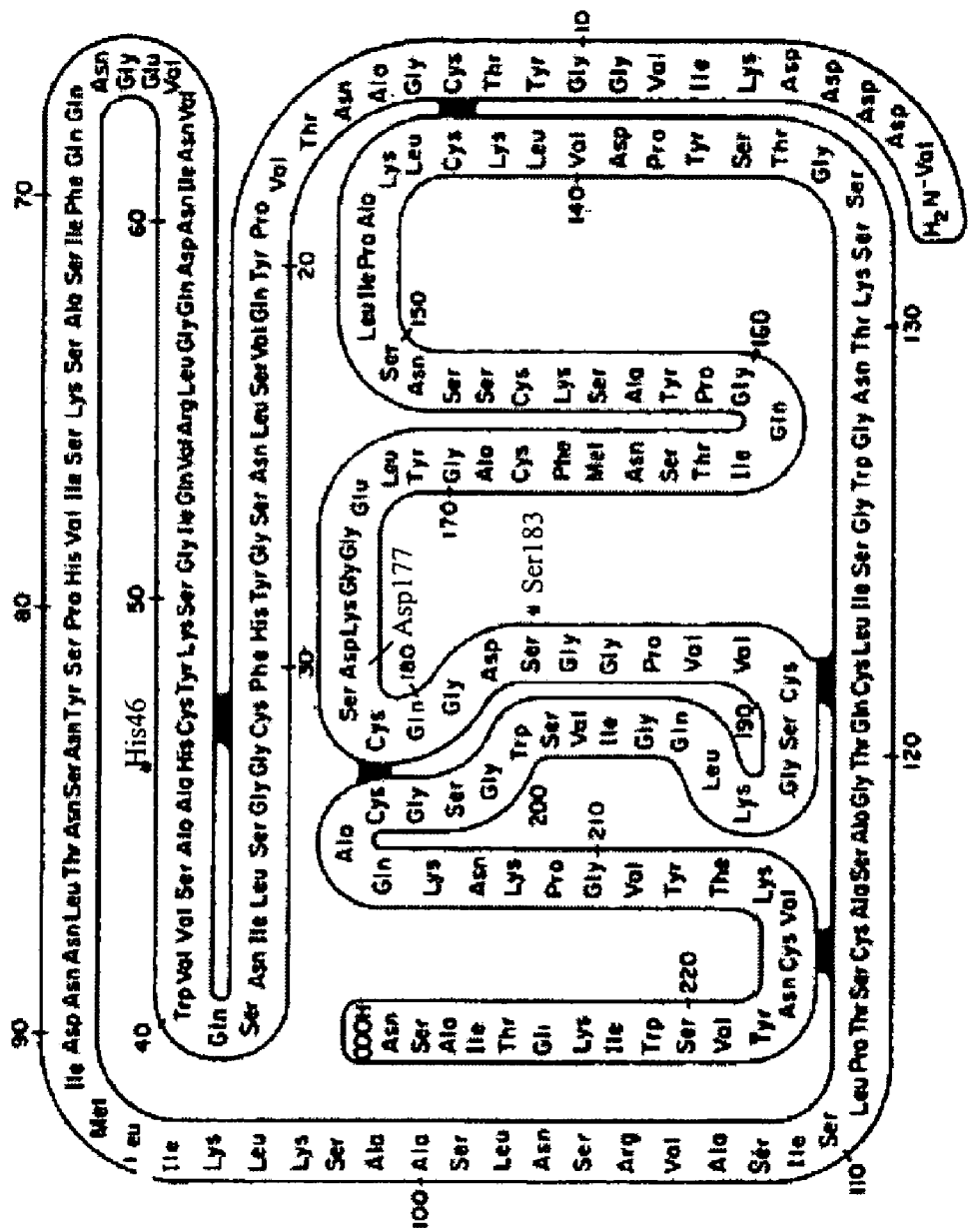
FIG. 1 illustrates the primary structure of trypsinogen.

The study of hydrolysis and condensation reactions in forming organic molecules is complicated. Specifically, such reactions are complicated in biosilicification due to the enhanced sensitivity of silica, silicates, and silicic acid to pH, concentration and temperature. Accordingly, the present invention overcomes such complications by utilizing a hydrolase enzyme to form structurally defined organic and more specifically organosilicon molecules. Specifically, as shown in the following reaction sequences, the hydrolase enzyme non-specifically promotes the hydrolysis of the organic reactant (A) to form an organic intermediate reactant (B) and subsequently selectively catalyzes the condensation of the organic intermediate reactant (B) to form the organic molecule (C).

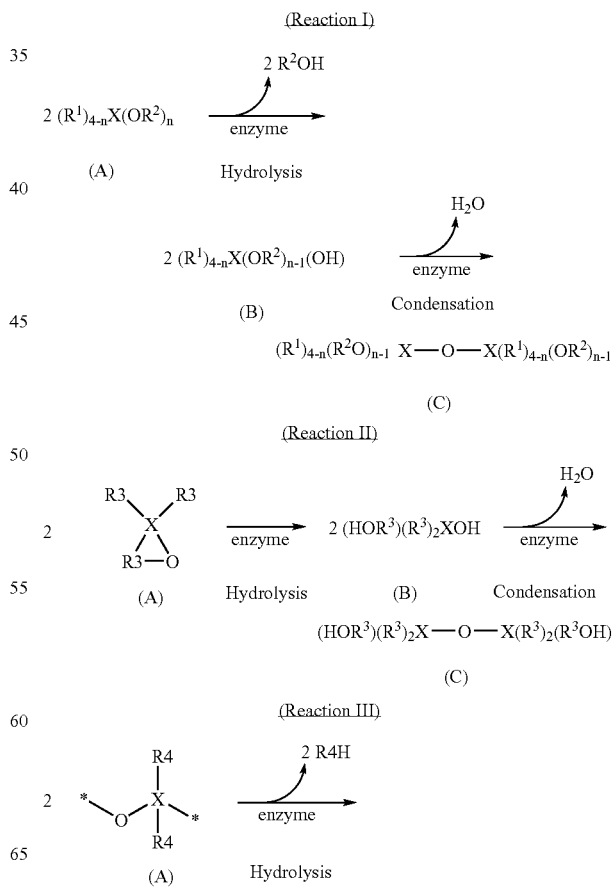

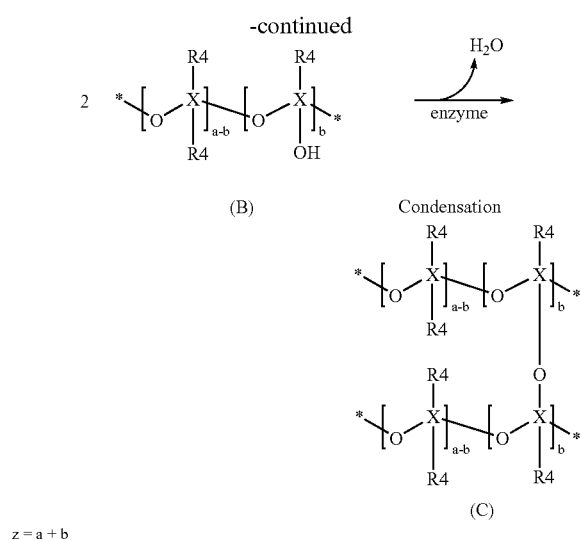

(B)

Condensation (C)

z = a + b

The organic reactants (A) of Reactions (I), (II) and (III) are acceptable substrates for the hydrolase enzyme to selectively catalyze hydrolysis and condensation of the organic reactant. The reactive sites of the organic reactant (A) comprise an electropositive atom (e.g. silicon or germanium) which facilitates the hydrolysis and condensation of the organic reactant (A) to ultimately form the organic molecule (C). Thus, structurally defined organic molecules may be formed using the organic reactants (A) of Reactions (I), (II) and (III).

One skilled in the art will appreciate the various inorganic elements X which may be utilized in the reactant, any of which may be employed herein. In one embodiment, X is selected from the group consisting of silicon and germanium. In addition, one skilled in the art will appreciate the various substituents which may be utilized for $R^1$, $R^2$, $R^3$, and $R^4$ in the above reactions, any of which may be employed herein. As such, it will be understood by those skilled in the art that the R groups of the organic structures do not have to be identical repeating units. Rather, the R groups may be independently chosen for each of the repeating units.

In one embodiment, $R^1$ is selected from the group consisting of alkyl, haloalkyl, unsaturated alkyl, aryl, alcohol, epoxy, ether, amine, $—(OXR^4{}_2)_y—OXR^4{}_3$, and a combination thereof, wherein $R^4$ is selected from the group consisting of alkyl, haloalkyl, unsaturated alkyl, aryl, hydrogen, hydroxy, alkoxy, alcohol, epoxy, ether, amine, $—OXR^4{}_2)_y—OXR^4{}_3$ and a combination thereof. In another embodiment, $R^2$ is selected from the group consisting of alkyl, hydrogen, ether and a combination thereof. In yet another embodiment, $R^3$ is selected from the group consisting of alkyl, unsaturated alkyl, aryl and hydrogen. In each embodiment detailed above, it will be further understood that alkyl, haloalkyl, unsaturated alkyl, and alkoxy may be substituents having one carbon or more than one carbon. Moreover, in the above reaction, n is defined as an integer from 0 to 4; y is defined as 0 or as an integer greater than 0; and z is 3 or an integer greater than 3. In addition, * as used throughout the application is indicative of a cyclic architecture, i.e., there is no defined end group.

The organic reactant (A) may be monofunctional or polyfunctional. For example, the formula of the organic reactant (A) may be selected from the group consisting of $(R^1)_4X$, $(R^1)_3X(OR^2)_1$, $(R^1)_2X(OR^2)_2$, $(R^1)_1X(OR^2)_3$ and $X(OR^2)_4$. Specific examples of di-functional organic reactants include, but are not limited to, $(CH_3)_2Si(OCH_3)_2$, $(CH_3)(CF_3CH_2CH_2)Si(OCH_3)_2$, $(C_6H_5)(CH_3)Si(OCH_3)_2$, and $(CH_3CH_2)_2Ge(OCH_2CH_3)_2$. Specific examples of tri- and tetra-functional organic reactants include, but are not limited to, $(CH_3)Si(OCH_2CH_3)_3$ and $Si(OCH_2CH_3)_4$, respectively. The organic reactant may also be linear, branched, resinous, or cyclic. In one embodiment, the distributions of linear, cyclic, and branched organic molecules may be filly hydroxylated after the initial interaction with the hydrolase enzyme. Specific examples of cyclic, linear, and branched organic reactants include, but are not limited to, 1,3,5,7-tetramethyl-1,3,5,7-tetramethoxy-cyclotetrasiloxane, 1,3-bis(hydroxy)tetramethyldisiloxane, and $[(HO)_2(CH_3)SiO]_3SiCH_3$, respectively.

Once a suitable organic reactant is identified, the organic reactant is contacted with a hydrolase enzyme in order to catalyze the formation of an organic molecule. The hydrolase enzyme may be derived from a bacterial, fungal, or mammalian source, or the hydrolase enzyme may be derived from any other suitable source. The enzyme is generally present as either a soluble solution or a heterogeneous suspension, and the enzyme may be lyophilized or immobilized. In a particular embodiment, the hydrolase enzyme is selected from the group consisting of lipase, protease, phosphoesterase, esterase, cutinase and a combination thereof. In another embodiment, the hydrolase enzyme comprises a lipase enzyme such as *Candida antarctica* lipase, *Candida antarctica* lipase B, *Rhizomucor miehei* lipase, wheat germ lipase or a combination thereof. In another embodiment, the hydrolase enzyme comprises a protease enzyme such as trypsin, papain, pepsin or a combination thereof.

In yet another embodiment, the hydrolase enzyme is trypsin or an enzyme that is at least 70% homologous with trypsin. Trypsinogen (FIGS. 1-2) is activated following the hydrolysis of the Lys6-Ile7 peptide bond and formation of β-trypsin (i.e. a disulfide cross-linked single polypeptide chain). Hydrophobic interactions with the new N-terminal isoleucine residue lead to the formation of regions such as the binding domain and oxyanion hole, which are known to participate in substrate recognition. As defined by these regions, trypsin selectively hydrolyses peptide bonds adjacent to basic residues (i.e. arginine>lysine>>natural amino acids). Following activation, autolysis of the Lys131-Ser132 and Lys176-Asp177 bonds leads to the formation of α-trypsin (i.e. a cross-linked two-chain structure) and pseudotrypsin (i.e. a cross-linked three-chain structure), respectively.

Figure 2:
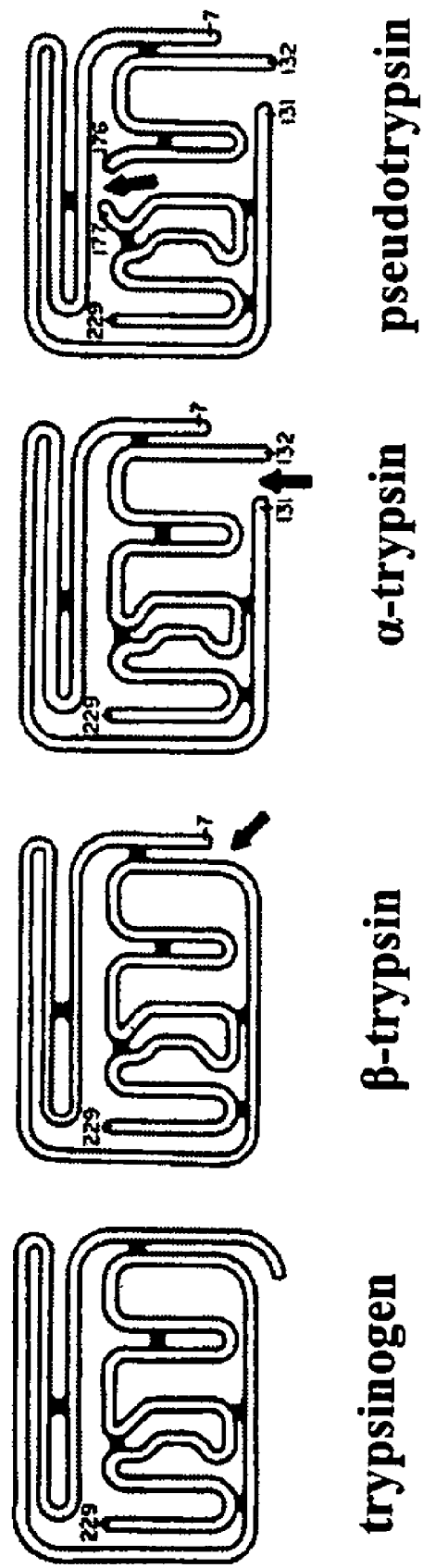
FIG. 2 illustrates the activation of trypsinogen.

Notably, the activation reactions and structural changes cause negligible alterations to the region of the catalytic triad (i.e. Ser183-His46-Asp177, FIG. 1 and SEQ ID NO:1). Based on these regions, trypsin has an affinity for basic residues in the substrate such as arginine and lysine due to an electrostatic attraction with an aspartate residue at the bottom of the pocket. Within these regions, non-covalent interactions participate in the stabilization of substrates throughout the enzymatic reactions. Commercial preparations of trypsin contain a mixture of predominately α- and β-trypsin as well as other digestive enzymatic contaminates. Based on the primary structure, the molecular weight of trypsin is 23,305. Furthermore, calcium may be added to the reaction to assist the hydrolase enzyme in reaction activity and specifically to promote stability of the enzyme.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The concentration, temperature and pH of the reaction may be varied as set forth in detail below. Specifically, the concentration of the hydrolase enzyme is generally greater than 1 mg/mL. In another embodiment, the concentration of the hydrolase enzyme is from about 10 mg/mL to about 80 mg/mL. In yet another embodiment, the concentration of the hydrolase enzyme is from about 20 mg/mL to about 60 mg/mL. In yet another embodiment, the concentration of the hydrolase enzyme is about 40 mg/mL. In one embodiment, the organic reactant to enzyme mole ratio is less than or equal to about 40000:1. In another embodiment, the organic reactant to enzyme mole ratio is less than or equal to about 1000:1.

The temperature of the reactions is generally between about 5° C. and 90° C. In another embodiment, the reaction is carried out at a temperature of between about 20° C. to about 50° C. In yet another embodiment, the reaction is carried out at a temperature about 25° C. The pH of the reaction is generally from about 5.0 to about 8.0. In one embodiment, the pH of the reaction is about 7.0.

In addition, the reactions may be performed under solventless (neat) conditions, or the reactions may be performed utilizing an aqueous solution or a solvent. Suitable solvents include, but are not limited to, water miscible organic solvent such as THF and acetonitrile, and relatively dry organic solvents such as toluene and hexane.

In order that the invention may be more readily understood, reference is made to the following examples, which are intended to be illustrative of the invention, but are not intended to be limiting in scope.

EXAMPLES

Materials

Protein and Peptides

*Aspergillus niger* lipase (Amano lipase A, #53,478-1), N-α-benzoyl-L-arginine ethyl ester (BAEE, #B4500), N-benzoyl-L-tyrosine ethyl ester (BTEE, #B6125), bovine pancreatic α-chymotrypsin (#C-4129), bovine pancreatic α-chymotrypsin treated with TLCK (#C3142), bovine pancreatic phospholipase A2 (P-8913), bovine pancreatic trypsin (#T4665), bovine pancreatic trypsin treated with TPCK (#T1426), bovine serum albumin (BSA, #B4287), *Candida antarctica* lipase (#62299), *Candida lipolytica* lipase (#62303), *Gadus morhua* trypsin (#T9906), hog stomach pepsin (#P7012), *Mucor javanicus* lipase (#62304), Novozyme 435® (immobilized *Candida antarctica* lipase B, ~1% protein, #53,732-2), papaya latex papain (#P4762), *Penicillium roqueforti* lipase (#62308), porcine β-globulins (#G2512), porcine pancreatic carboxypeptidase B (#C9584), porcine pancreatic elastase (#E0258), porcine pancreatic lipase (#L-3126), porcine pancreatic trypsin (#T0303), protease (subtilisin Carlsberg, #P8038), *Pseudomonas cepacia* lipase (Amano lipase PS, #53,464-1), *Pseudomonas fluorescens* lipase (#62321), *Rhizomucor miehei* lipase (#62291), trypsin inhibitor from Glycine max (Popcorn inhibitor from soybean, #T9128), trypsin-chymotrypsin inhibitor from soybean (Bowman-Birk inhibitor, #T9777), N-α-p-tosyl-L-lysine chloromethyl ketone hydrochloride,(TLCK, #T7254), N-tosyl-L-phenylalanine chloromethyl ketone (TPCK, #T4376), wheat germ lipase (#62306) were purchased from Sigma-Aldrich (St. Louis, Mo.). Bovine kidney cathepsin L (#219418), human liver cathepsin L (#219402), and *Paramecium tetraurelia* cathepsin L (#219412) were purchased from Calbiochem®, EMD Biosciences (San Diego, Calif.). Recombinant bovine trypsin expressed in maize (#TRY, CAS #9002-07-7) was purchased from ProdiGene (College Station, Tex.).

Water

Ultra pure water was obtained from a Milli-Q system at the Dow Corning Corporation (Midland, Mich.). Trizma® preset crystals pH 7.0 (Tris-HCl, #T3503), pH 7.5 (Tris-HCl, #T4128), pH 7.8 (Tris-HCl, #T4503), pH 8.0 (Tris-HCl, #T4753), and pH 9.0 (Tris-HCl, #T6003) were purchased from Sigma-Aldrich. Buffer solutions pH 4.00 (potassium biphthalate, #SB101), pH 5 (sodium hydroxide-citric acid, #A015860101), pH 6.00 (monobasic potassium phosphate-sodium hydroxide, #SB104), and pH 10.00 (potassium carbonate-potassium borate-potassium hydroxide, #SB115) were purchased at Fisher Scientific (Pittsburgh, Pa.).

Organic and Inorganic Molecules

Acetonitrile (#A996-4), acetone (#A929-4), phosphorous pentoxide (#A244), 2-propanol (#A451-4), tetrahydrofuran (#T427-1), and toluene (#T291-4) were purchased from Fisher Scientific. Acetic acid (#A6283), calcium chloride (#C3881), dodecane (#44010), ethanol (#45,984-4), hexanol (#H13303), hydrochloric acid (#33,925-3), lithium aluminum hydride (#19,987-7), sodium chloride (#20,443-9), and sodium hydrogencarbonate (#34,094-4) were purchased from Sigma-Aldrich. Tetraethylene glycol monomethyl ether (#T1372) was purchased from TCI America (Portland, Oreg.). HPLC grade organic solvents were used throughout the examples Silicon-Based Molecules Trimethylsilanol (CAS #1066-40-6, #12848-72), heptamethylhydroxytetracyclosiloxane (#11050-134B), hexamethylcyclotrisiloxane (#E-459-80, cut #3), octamethylcyclotetrasiloxane (#E-1927-93-2, lot #2), 1,3,5-trimethyl-1,3,5-tri (3,3,3-trifluoropropyl)cyclotrisiloxane (LS Trimer), 1,3,5,7-tetramethyl-1,3,5,7-tetra(3,3,3-trifluoropropyl) cyclotetrasiloxane (#H-1387-145), and 2,4,6,8-trimethyl-2, 4,6,8-tetraphenyl-cyclotetrasiloxane (#1923-44A) were obtained at the Dow Corning Corporation. 3-Aminopropyldimethylethoxysilane (#SIA0603.0), bis(trimethylsilyl)acetamide (#SIB 1846.0), 1,1-dimethyl-1-sila-2-oxacyclohexane (#SID4234.0), 3-glycidoxypropyldimethylethoxysilane (#SIG5825), hexamethyldisiloxane (#SIH6115.0), trimethylethoxysilane (#SIT8515.0), and triphenylethoxysilane (#SIT8652.0) were purchased at Gelest, Inc. (Tullytown, Pa.). Hexamethyldisilazane (#37921-2) and tetraethoxysilane (#23620-9) were purchased at Sigma-Aldrich. Phenyldimethylethoxysilane (#P0161) was purchased from United Chemical Technologies, Inc. (Bristol, Pa.). Methyltriethoxysilane (#M9050) was purchased from Huls America, Inc. (Bristol, Pa.).

Synthesis of Trimethylalkoxysilane

Two trimethylalkoxysilanes were synthesized with polar and non-polar leaving groups. Tetraethylene glycol monomethyl ether (TGME) and hexanol were silylated with bis(trimethylsilyl)acetamide to obtain the target polar ($Me_3SiO(CH_2CH_2O)_4CH_3$) and non-polar ($Me_3SiOC_6H_{13}$) silanes, respectively.

Example 1

Biocatalysis Study

This study was directed to a quantitative test of the ability of enzymes to catalyze the formation of siloxane bonds during the in vitro hydrolysis and condensation of alkoxysilanes. Since mono-functional silanes were chosen as reactants during the formation of molecules with a single siloxane bond, rigorous procedures were established to prepare glassware, as well as isolate and quantitatively analyze the reaction products by gas chromatography (GC).

The measure of extraction efficiency was defined as the percent yield of reactants and products. The mass balances were equal to the sum total of the extraction values. Based on the chromatographic results, the extraction efficiencies of THF at 25° C. were excellent in comparison to diethylether, methylene chloride and toluene. Based on two extractions, mass balances greater than 98% were routinely obtained by THF.

Figure 3:
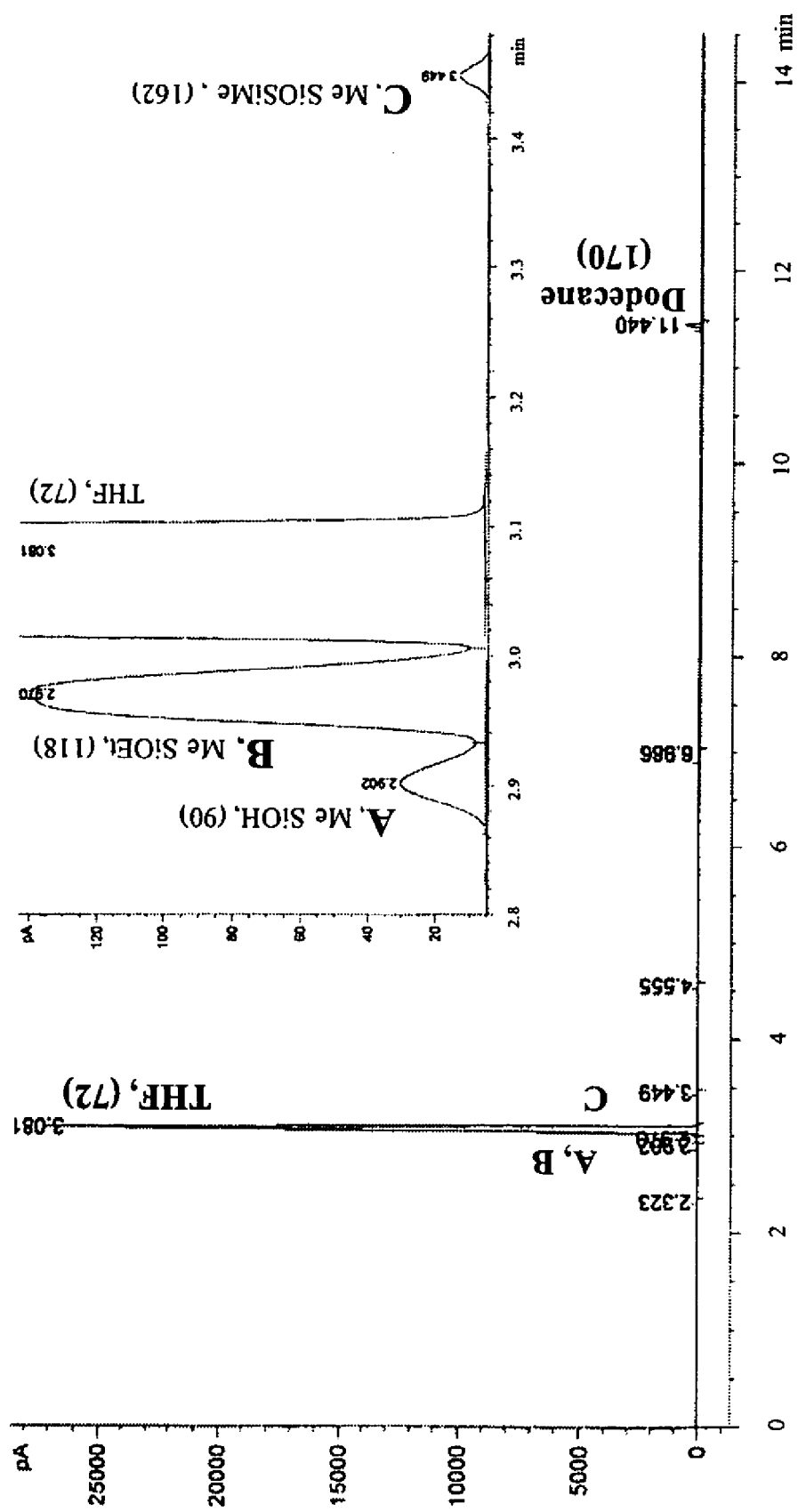
FIG. 3 illustrates a GC-FID chromatogram of a trimethylethoxysilane negative control reaction.

Based on triplicate measurements, the response factors for the analytes were calculated and determined to be linear as a function of concentration over three orders of magnitude (i.e. 0.1-10% (w/w)). The alkoxysilane, silanol, and disiloxane analytes were chromatographically resolved as illustrated in FIG. 3. The ability to resolve these analytes was necessary to differentiate between the role of an enzyme in the hydrolysis and condensation reactions during biosilicification. Comparatively, given the limitations of the product and resultant analyses, the *Tethya aurantia* marine sponge (i.e. silicatein) and *Equisetum telmateia* plant (i.e. biopolymer) studies including a silicatein-mimetic approach (i.e. diblock polypeptides) were not able to differentiate between the role of the proteins or polypeptide in the hydrolysis and condensation reactions during biosilicification.

Example 2

Enzyme-Catalyzed Condensation Study

This study was directed to an enzyme screen with trimethylsilanol in order to evaluate the ability of various enzymes to catalyze the formation of a siloxane bond. Based on the similarities of the proteins isolated from the *Tethya aurantia* marine sponge (silicatein), *Cylindrotheca fusiformis* diatom (silaffin), and *Equisetum telmateia* plant (biopolymer extract), a series of lipases and serine-proteases were selected as homologous proteolytic enzymes. In addition to catalyzing comparable reactions (i.e. the hydrolysis of amide and/or ester bonds), the active sites in the hydrolase enzymes are composed of similar serine-histidine-aspartate catalytic triads. In comparison to control reactions, the mammalian, fungal, and bacterial lipases and proteases detailed in Table 1 were screened with trimethylsilanol. In this study, control reactions were defined as non-enzymatic reactions. Specifically, experiments conducted in the absence of a protein were defined as negative control reactions. Proteinaceous molecules such as bovine serum albumin and porcine γ-globulins were used to study non-specific protein catalysis.

TABLE 1

| Enzyme screen. | | |
|---|---|---|
| Mammalian | Fungal | Bacterial |
| bovine pancreatic α-chymotrypsin | *Aspergillus niger* lipase | *Pseudomonas cepacia* lipase |
| bovine pancreatic phospholipase A2 | *Candida antarctica* lipase | *Pseudomonas fluorescens* lipase |
| bovine pancreatic trypsin | *Candida antarctica* lipase B[1] | |
| porcine pancreatic lipase | *Candida lipolytica* lipase | |
| | *Mucor javanicus* lipase | |
| | *Penicillium roqueforti* lipase | |
| | *Rhizomucor miehei* lipase | |
| | wheat germ lipase | |

[1]*Candida antarctica* lipase B was immobilized on acrylic resin beads (Novozyme ® 435).

Prior to reaction, the glass vials were rinsed with acetone (×2) and ethanol (×2), dried, and silylated with hexamethyldisilazane (1 mmol) in the presence of acetic acid (0.2 mmol) for 30 m at 25° C. Subsequently, the vials were rinsed with ethanol (×2) and dried in an oven at 110 ° C. The silylated glass vials were confirmed not to contaminate the reactions with trimethylsilanol or hexamethyldisiloxane.

The reactions were formulated with a 5:1 trimethylsilanol (225 mg) to protein (45 mg lipase, protease, or BSA) weight ratio in 1.3 mL toluene or 1.1 mL water. Toluene was dried over lithium aluminum hydride ('dry toluene', 11 ppm water) and hydrated with Milli-Q water ('wet toluene', 467 ppm water). Karl Fischer titrations were performed on an Aquatest IV titrator (Photovolt Corporation, New York, N.Y.) to measure the water content in toluene. Milli-Q water ('water') was buffered with 50 mM Tris-HCl buffer, pH 7.0 ('buffered pH 7'). The estimated solubility of trimethylsilanol in water is 4.2% (i.e. 42.56 mg/mL). Based on the formulation, the two-phase reactions conducted in water were saturated with trimethylsilanol (~200 mg/mL). The closed (screw capped) reactions were conducted in inert glass vials at 25° C. with magnetic stirring for 6 days. The reaction products were isolated and quantitatively analyzed by GC. Prior to analysis, the aqueous reactions were extracted (×2) with THF in the presence of NaCl and filtered through a Whatman Autovial® 5 0.45 μm Teflon® filter (#AV115NPUORG).

The results are summarised in Table 2. In comparison to negative control and non-specific protein (i.e. BSA) reactions, select lipases as well as trypsin and α-chymotrypsin were observed to catalyse the condensation of trimethylsilanol during the formation of hexamethyldisiloxane under mild conditions. The enzymes checked (✓) in Table 2 were determined to catalyse the condensation of greater than ten times more trimethylsilanol than the negative control reactions; as well as, greater than three or ten times more trimethylsilanol than the BSA reactions in organic and aqueous media, respectively. Conversely, the ability of the unchecked enzymes in Table 2 to catalyse the model condensation reaction was not substantially different than the control reactions. In review, the relative rate of condensation increased in water. As opposed to lipases, proteases will only interact with water soluble substrates. The estimated water solubility of trimethylsilanol is 4.2% (i.e. 42.56 mg/mL).

TABLE 2

Enzyme-catalyzed condensation study after six days.

| Enzyme | Dry Toluene | Wet Toluene | Water | Buffered pH 7 |
|---|---|---|---|---|
| negative control | | | | |
| bovine serum albumin | | | | |
| Aspergillus niger lipase | | | | |
| Candida antarctica lipase | | | ✓ | |
| Candida antarctica lipase B[1] | | | ✓ | |
| Candida lipolytica lipase | | | | |
| α-chymotrypsin | ✓ | ✓ | ✓ | ✓ |
| Mucor javanicus lipase | | | | |
| Penicillium roqueforti lipase | | | | |
| phospholipase A2 | | | | |
| porcine pancreatic lipase | | | | |
| Pseudomonas cepacia lipase | | | | |
| Pseudomonas fluorescens lipase | | | | |
| Rhizomucor miehei lipase | | | ✓ | |
| trypsin | ✓ | ✓ | ✓ | ✓ |
| wheat germ lipase | | ✓ | ✓ | |

[1]Candida antarctica lipase B was immobilized on acrylic resin beads (Novozyme ® 435).

Example 3

Protease-Catalyzed Silanol Reactions

Based on the exceptional activity of trypsin and α-chymotrypsin from bovine pancreas (Table 2), protease enzymes were identified as target catalysts. Consequently, a series of serine-, cysteine-, aspartic-, and metallo-proteases were selected in order to evaluate their ability to catalyze the formation of a molecule with a siloxane bond in a neutral medium (pH 7.0) (Scheme 1).

Scheme 1:
Protease-catalyzed condensation of trimethylsilanol.

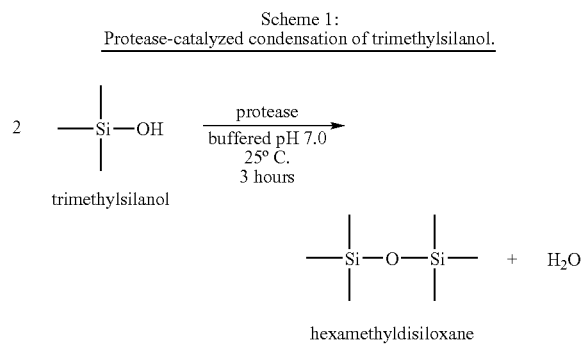

In comparison to control reactions, the ability of the proteases detailed in Table 3 to catalyse siloxane condensation was screened with trimethylsilanol. Comparatively, the original reactions conducted in the enzyme-catalysed condensation study were performed for six days versus three hours in this study.

TABLE 3

Protease screen.

| Serine-Protease | Cysteine-Protease | Aspartic-Protease | Metallo-Protease |
|---|---|---|---|
| α-chymotrypsin (bovine pancreatic) | cathepsin L (bovine kidney) | pepsin (hog stomach) | carboxypeptidase B (porcine pancreas) |
| elastase (porcine pancreatic) | cathepsin L (human liver) | | |
| subtilisin Carlsberg (B. licheniformis) | cathepsin L (Paramecium tetraurelia) | | |
| trypsin (bovine pancreatic) | papain (papaya latex) | | |

Prior to reaction, the glass vials were silylated. The reactions were formulated with a 4:1 trimethylsilanol (80 mg) to protein (20 mg protease, BSA, or 65-globulins) weight ratio (~1000:1 silanol to protease mole ratio) in 0.5 mL of 50 mM Tris-HCl buffered Milli-Q water, pH 7.0.

Figure 4:
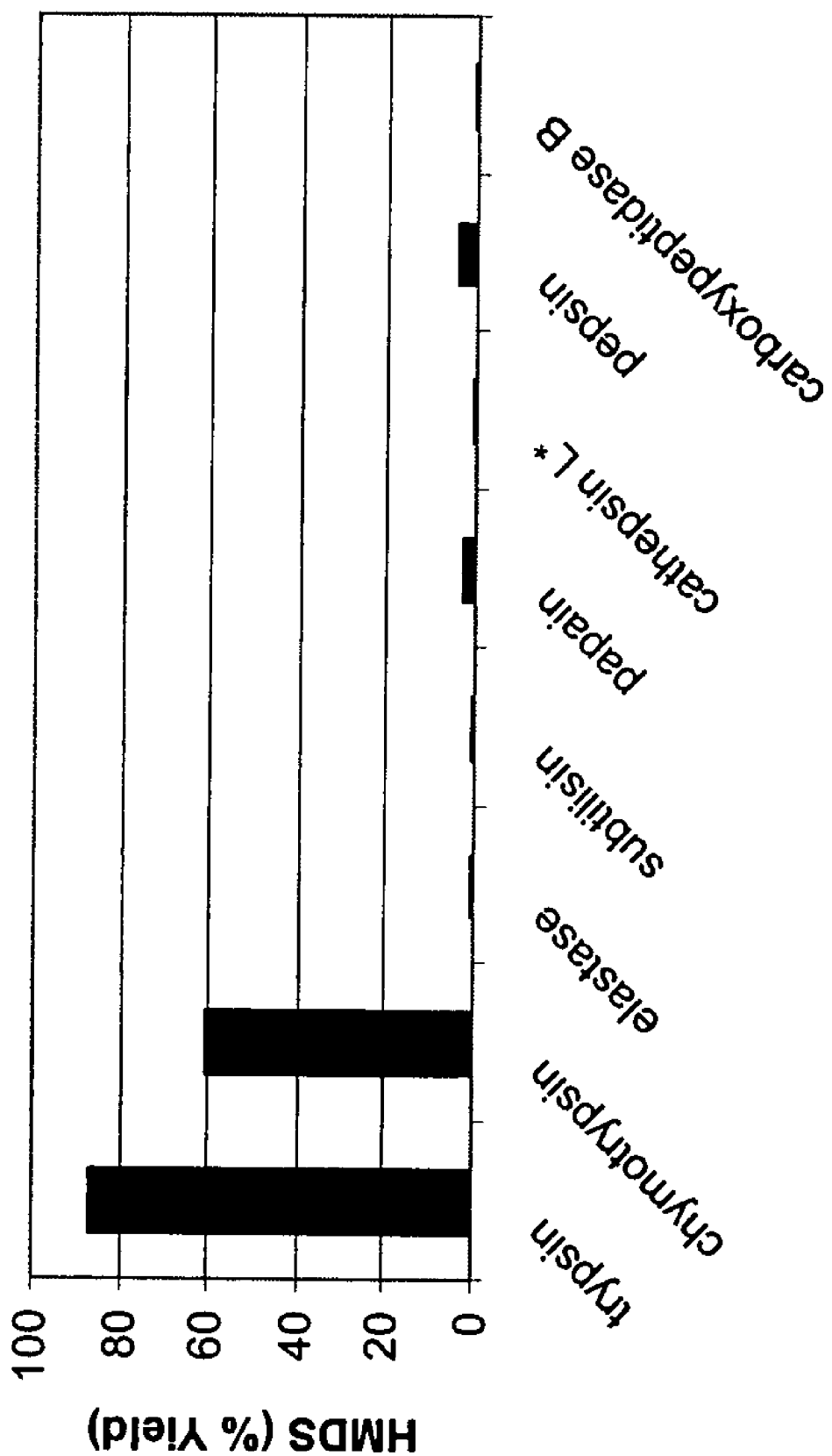
FIG. 4 illustrates a protease-catalyzed condensation study after three hours.

Based on the estimated solubility of trimethylsilanol in water (42.56 mg/mL), the concentration of trimethylsilanol (~160 mg/mL) saturated the aqueous media and created two-phase reaction mixtures. The reaction products were isolated and quantitatively analyzed by GC as illustrated in FIG. 4. Prior to analysis, the aqueous reactions were extracted (×2) with THF in the presence of NaCl and filtered through a Whatman Autovial® 5 0.45 μm Teflon® filter.

Trypsin and α-chymotrypsin preferentially catalyzed the condensation of trimethylsilanol under mild conditions. A neutral medium (pH 7.0) was used to differentiate enzymatic vs. chemical catalysis. Given the specificity in the catalytic regions, the proteases are substrate selective. Trimethylsilanol was chosen as a model silanol to study the role of an enzyme in the formation of molecules with a single siloxane bond. Notably, three sources of cathepsin L did not catalyze the condensation reaction. In contrast, although silicatein was documented to be highly homologous with cathepsin L, silicatein catalyzed the formation of particulate silica and silsesquioxanes. The activities of the enzymes depend upon the functionality of the non-natural organosilicon substrates.

Figure 5:
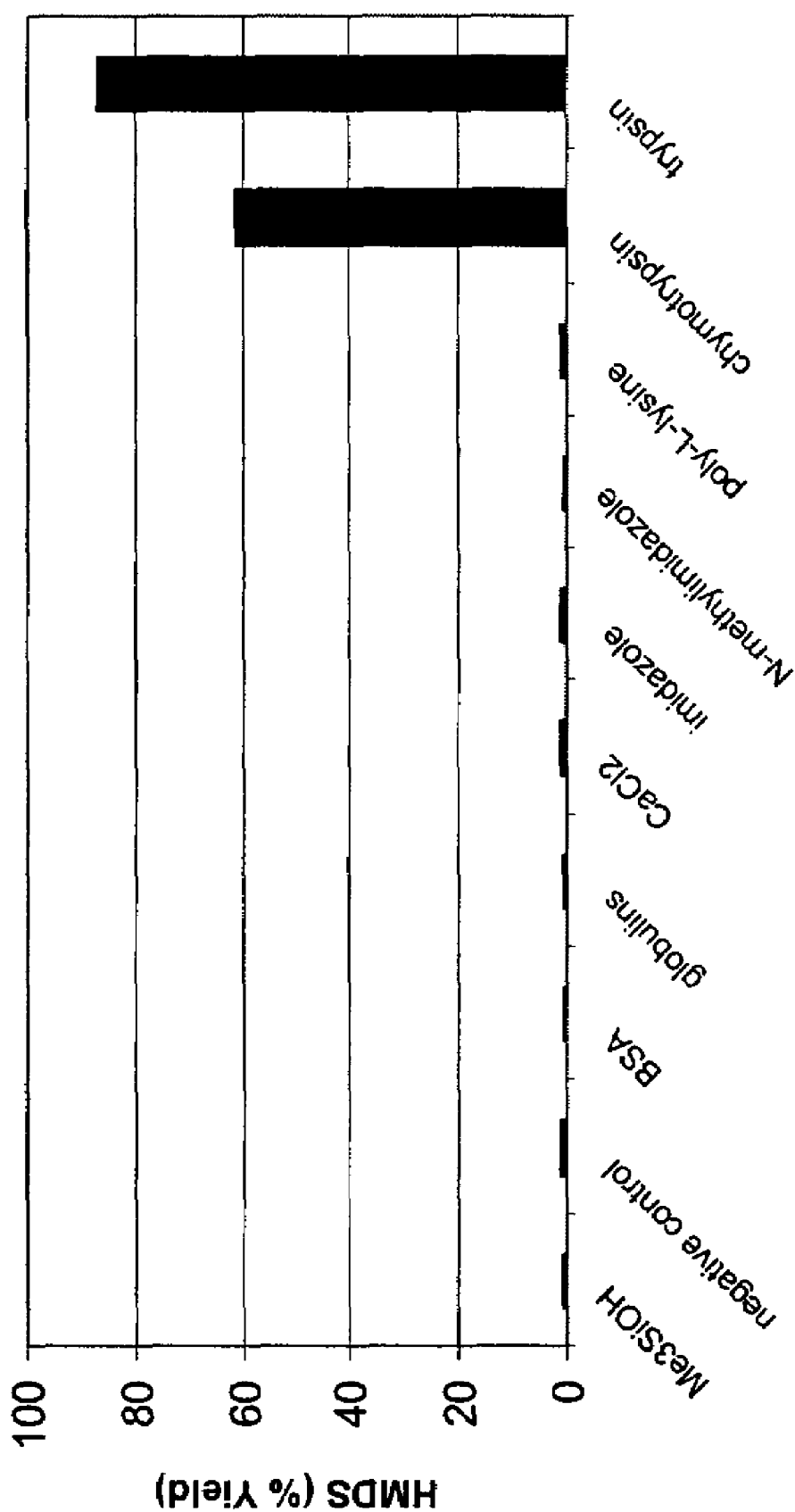
FIG. 5 illustrates the condensation control reactions after three hours.

Substantial condensation of trimethylsilanol was not observed in the negative control, non-specific protein (i.e. BSA, γ-globulins), small molecule (i.e. $CaCl_2$, imidazole, N-methylimidazole), and polypeptide (i.e. poly-L-lysine) reactions in comparison to the raw material (FIG. 5). In addition to the proteins, the small molecules were chosen to independently evaluate non-specific catalysis based on the functionality of catalytically active trypsin. Since calcium is required to maximize tryptic activity and stability, trypsin may be treated with calcium chloride. Analogous to the amino-functional residues on the surface of trypsin, imidazole, N-methylimidazole, and poly-L-lysine were included to assess base catalysis in a neutral medium. Similarly, BSA and poly-L-lysine were not observed to catalyze the polycondensation of tetraethoxysilane in aqueous media (pH=6.8).

Example 4

Impurity Study

Figure 6:
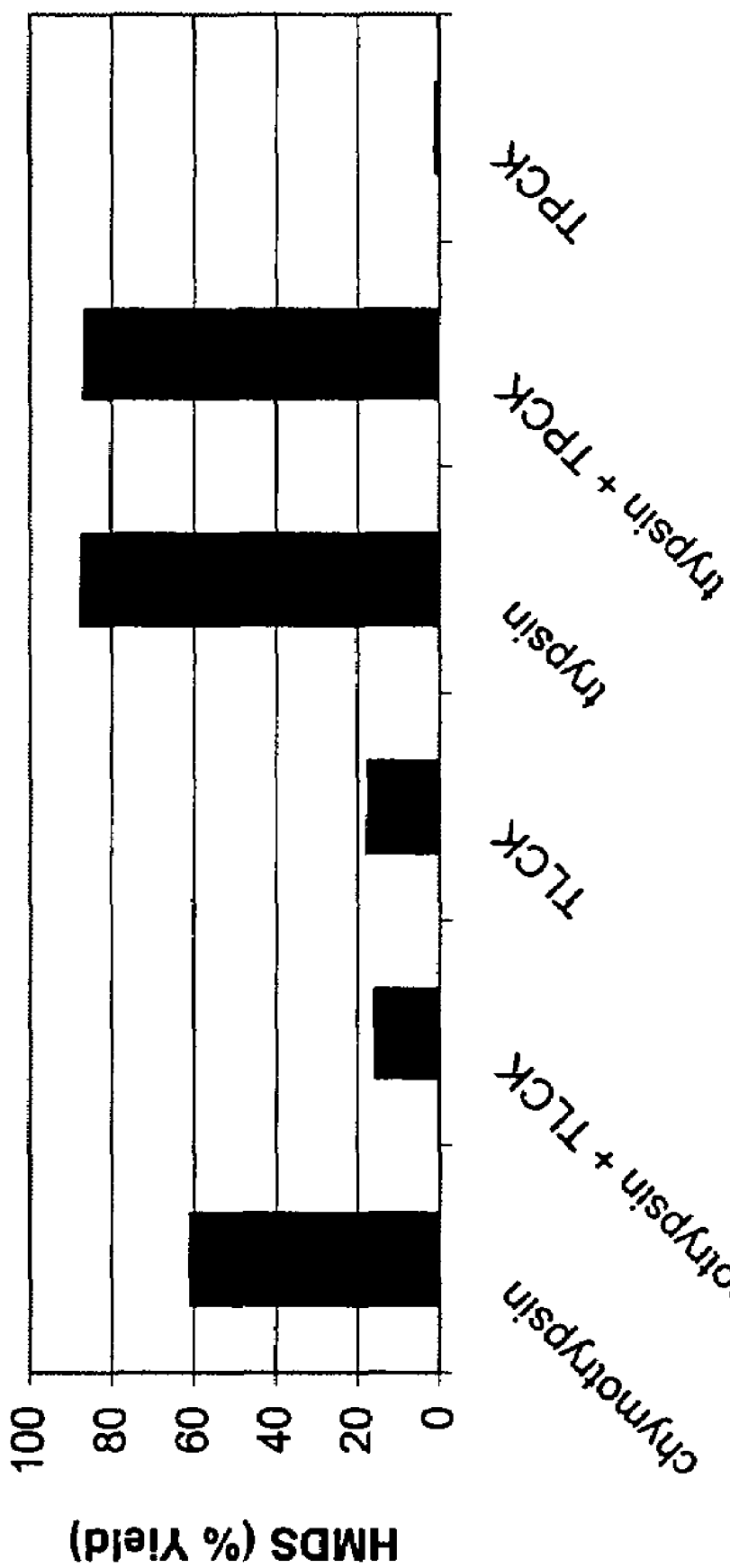
FIG. 6 illustrates α-chymotrypsin and trypsin impurity study.

Given an enhanced preference for basic residues such as arginine and lysine, N-α-p-tosyl-L-lysine chloromethyl ketone hydrochloride selectively and irreversibly inhibits trypsin activity without affecting α-chymotrypsin activity. TLCK inhibits trypsin by alkylating the histidine residue in the catalytic triad. After treating α-chymotrypsin with TLCK, the product yield significantly decreased in the replicate condensation experiment (FIG. 6).

Based on the product yield of the TLCK control reaction (FIG. 6), α-chymotrypsin did not catalyse the condensation of trimethylsilanol. Alternatively, trypsin treated with N-tosyl-L-phenylalanine chloromethyl ketone, an irreversible chymotrypsin inhibitor, was used to complement the TLCK treated α-chymotrypsin experiment. Given the specificity of chymotrypsin to hydrophobic residues such as phenylalanine, TPCK inhibited chymotrypsin by alkylating the histidine residue in the catalytic triad. Based on the chromatographic results (FIG. 6) and the inactivity of elastase (FIG. 4), trypsin as opposed to α-chymotrypsin was determined to catalyse the condensation of trimethylsilanol. Furthermore, the exceptional activity of trypsin and α-chymotrypsin observed in the original enzyme-catalysed condensation study (Table 2) was due to a tryptic impurity.

Example 5

Trypsin-Catalysed Condensation of Silanols

Prior to the reactions, the glass vials were silylated. The reaction products were isolated and quantitatively analysed by GC. Prior to analysis, the aqueous reactions were extracted (×2) with THF in the presence of NaCl and filtered through a Whatman Autovial® 5 0.45 µm Teflon® filter. In these studies, control reactions are defined as non-enzymatic reactions. Specifically, experiments conducted in the absence of a protein are defined as negative control reactions.

Proteinaceous Inhibition Study

A proteinaceous inhibition study was conducted to investigate the role of the enzymatic active site in the model silanol condensation reaction. Specifically, trypsin and α-chymotrypsin were inhibited with two distinctly different natural polypeptide inhibitors from soybean: a trypsin-chymotrypsin inhibitor (i.e. the Bowman-Birk Inhibitor, BBI) and a trypsin inhibitor from Glycine max (i.e. the Kunitz soybean trypsin inhibitor or Popcorn inhibitor, PCI).

The soybean inhibitors are highly stable proteins with well-defined inhibitory sites. Although the proteinaceous inhibitors originate from the same source, the amino acid sequences, tertiary structures, and properties of the polypeptides are different. The BBI and PCI proteins contain 71 (MW=7,975) and 181 (MW=21,700) amino acids, respectively. BBI contains dual independent regions that selectively inhibit trypsin and chymotrypsin. The reactive sites within these regions are defined as Lys16-Ser17 (trypsin) and Leu43-Ser44 (chymotrypsin). The kinetics and equilibria of the inhibition reactions are independent. PCI selectively inhibits trypsin through interactions with an Arg63-Ile64 reactive site.

Figure 7:
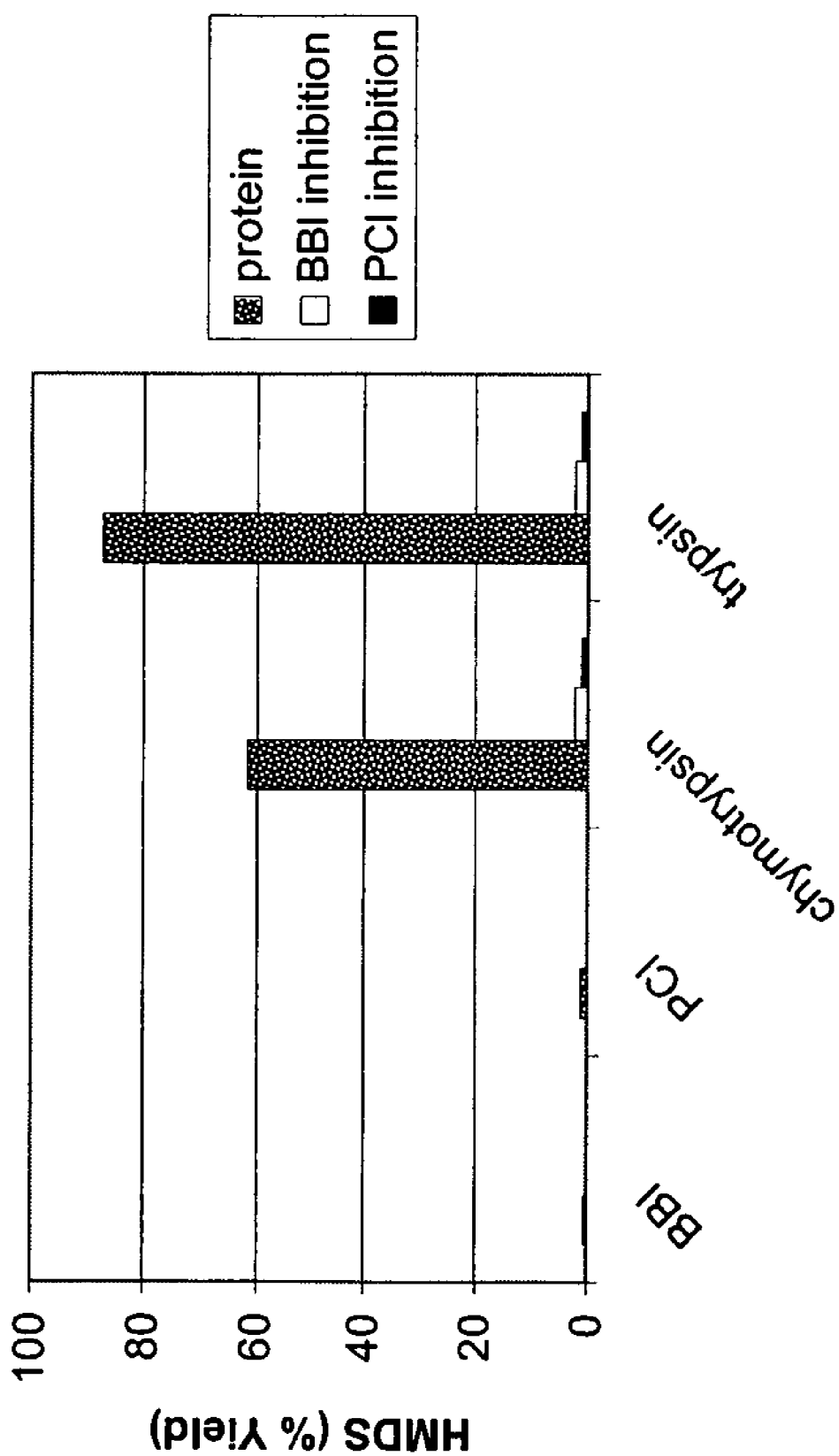
FIG. 7 illustrates a proteinaceous inhibition of the condensation of trimethylsilanol.

Prior to reaction, the enzymes were inhibited with excess inhibitor (i.e. >1:1 (w/w) or 4:1 BBI to protease and 2:1 PCI to protease mole ratios, respectively) in stirred neutral media (pH 7.0) for two hours before the addition of trimethylsilanol. The reactions were formulated with a 4:1 monomer to enzyme weight ratio (~1000:1 silanol to protease mole ratio) and conducted at 25° C. for three hours. The reaction products were isolated and quantitatively analyzed by GC (FIG. 7).

Based on standard enzymatic activity assays, trypsin was fully inhibited with BBI (98%) and PCI (91%), while α-chymotrypsin was partially inhibited with BBI (63%). In comparison to the control reactions, the proteinaceous inhibitors completely inhibited the protease-catalyzed condensation reactions. Since α-chymotrypsin was inhibited by PCI, the presence of trypsin in α-chymotrypsin was confirmed. In addition, condensation was not observed despite the partial inhibition of α-chymotrypsin with BBI. While not wishing to be bound by theory, it appears that the tertiary structure, functionality of the active site, and catalytic triad of trypsin are directly involved in the in vitro condensation of trimethylsilanol.

Temperature Study

Figure 8:
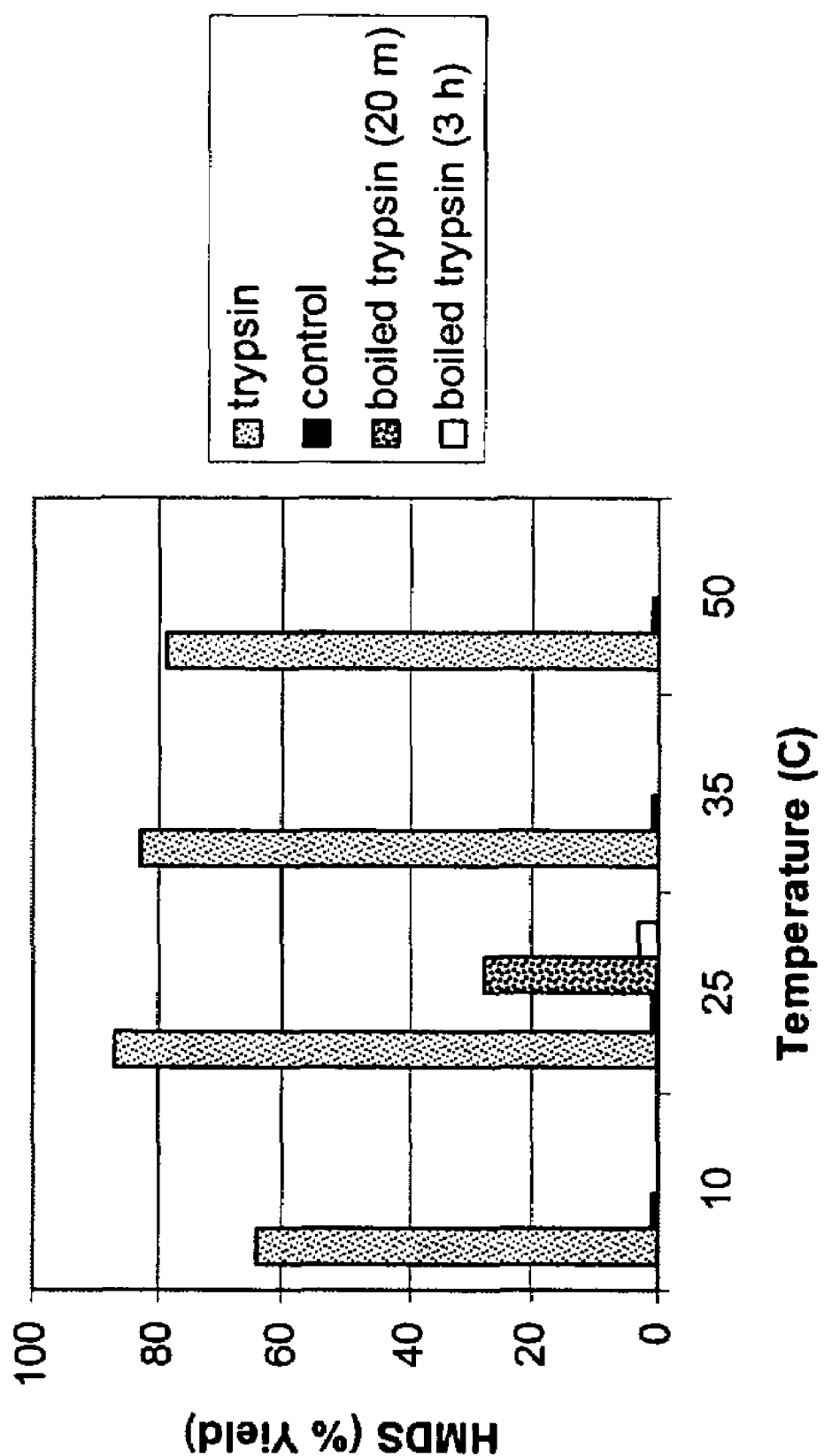
FIG. 8 illustrates the effect of temperature on the trypsin-catalyzed condensation of trimethylsilanol.

The effect of temperature on trypsin as well as the enzyme-catalyzed condensation reaction was studied. Prior to reaction, buffered aqueous solutions (pH 7.0) of trypsin were stirred and equilibrated at set temperatures in a thermostated water bath (+/−0.1° C.) for 20 minutes. The reactions were formulated with a 4:1 monomer to enzyme weight ratio (~1000:1 silanol to trypsin mole ratio) and conducted at set temperatures for three hours. In the thermal denaturation experiments, trypsin was boiled for 20 minutes and three hours in 50 mM Tris-HCl buffered Milli-Q water (pH 7.0), independently, before performing the condensation reaction at 25° C. The reaction products were isolated and quantitatively analyzed by GC (FIG. 8).

In comparison to the control reactions, trypsin appears to be catalytically active over a broad temperature range. The optimum temperature of the reaction was approximately 25° C. After boiling the solutions of trypsin (40 mg/mL) for different periods of time (i.e. 20 minutes vs. 3 hours), the rates of the trypsin-catalyzed condensation reactions decreased due to the degree of thermal denaturation. Although enzymatic reaction rates may increase with temperature, elevated temperatures have been reported to reversibly unfold and irreversibly inactivate enzymes including trypsin in water due to decomposition.

Figure 9:
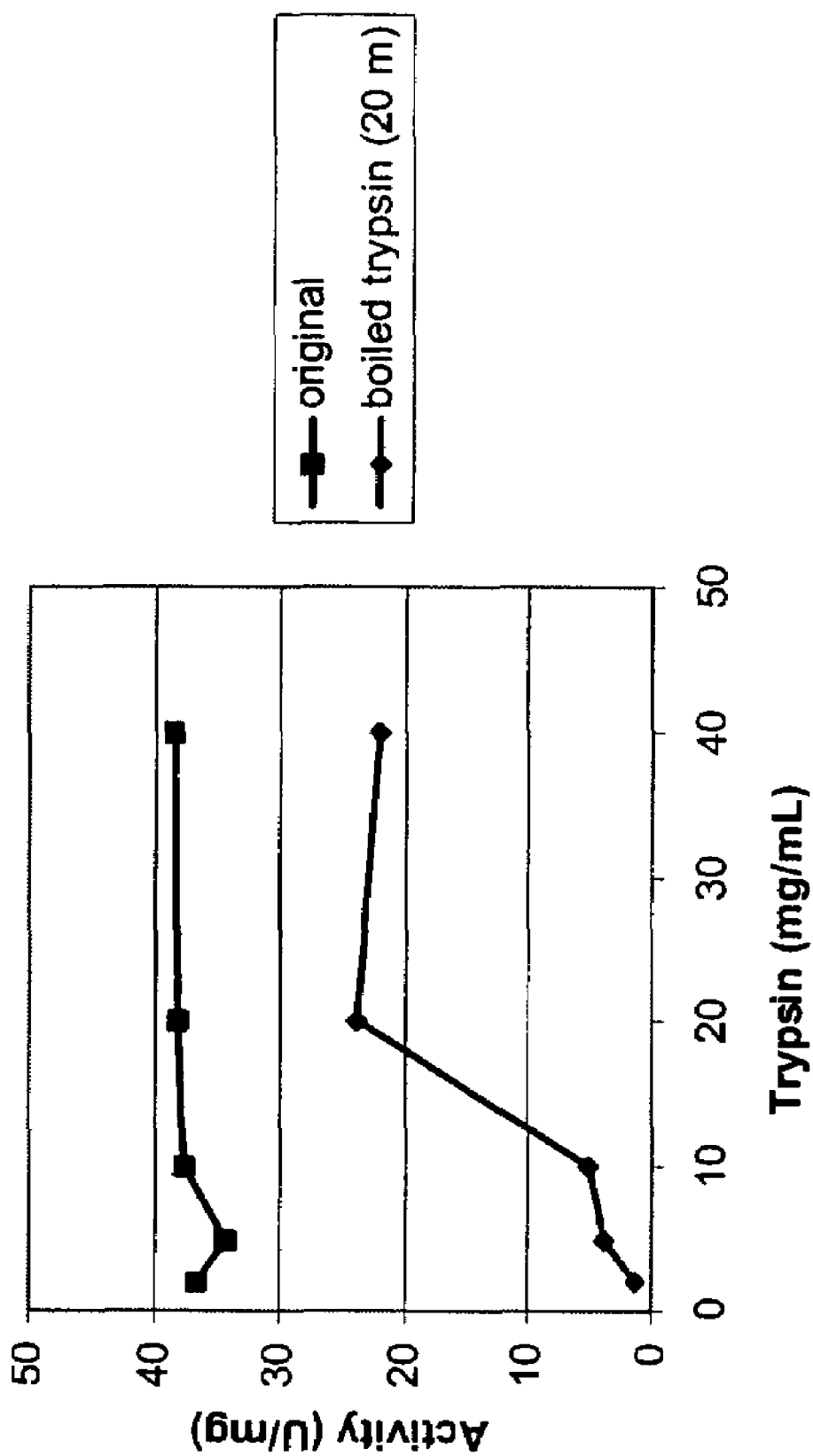
FIG. 9 illustrates a study of the thermal denaturation of trypsin in neutral media as a function of the concentration of trypsin.

Since the rate of reaction was dependent on the degree of thermal denaturation, a natural substrate, N-α-benzoyl-L-arginine ethyl ester (BAEE), was used to study the activity of boiled tryptic solutions as a function of concentration in neutral media (pH 7.0). Different concentrations of trypsin (i.e. 2-40 mg/mL) were prepared in 0.5 mL of 50 mM Tris-HCl buffered Milli-Q water (pH 7.0). The solutions were boiled for 20 minutes before measuring the activity of the boiled trypsin by recording the change in absorbance at 253 nm due to the formation of N-α-benzoyl-L-arginine. The spectrophotometric activity data is illustrated in FIG. 9.

As measured by the rate of hydrolysis of BAEE, the activity of the boiled tryptic solutions decreased at lower concentrations due to increased denaturation. Comparatively, the relative decrease in the rate of silanol condensation (FIG. 8) correlated with the enhanced stability of trypsin at higher protein concentrations (FIG. 9). Based on a thermogravimetric analysis, trypsin experienced a small mass loss (5%) from room temperature to 100° C. and a critical mass loss at 225° C. The thermal profile supports the potential loss of water prior to physical decomposition. Visually, the recovered sample was significantly charred. In a differential thermogram, an irreversible endothermic melt (Tm) was observed at 40° C. due to a crystalline or ordered phase in the enzyme. While not wishing to be bound by theory, it appears that trypsin was irreversibly denatured due to the lack of a replicate endothermic melt during the second heating cycle.

Time Study

Figure 10:
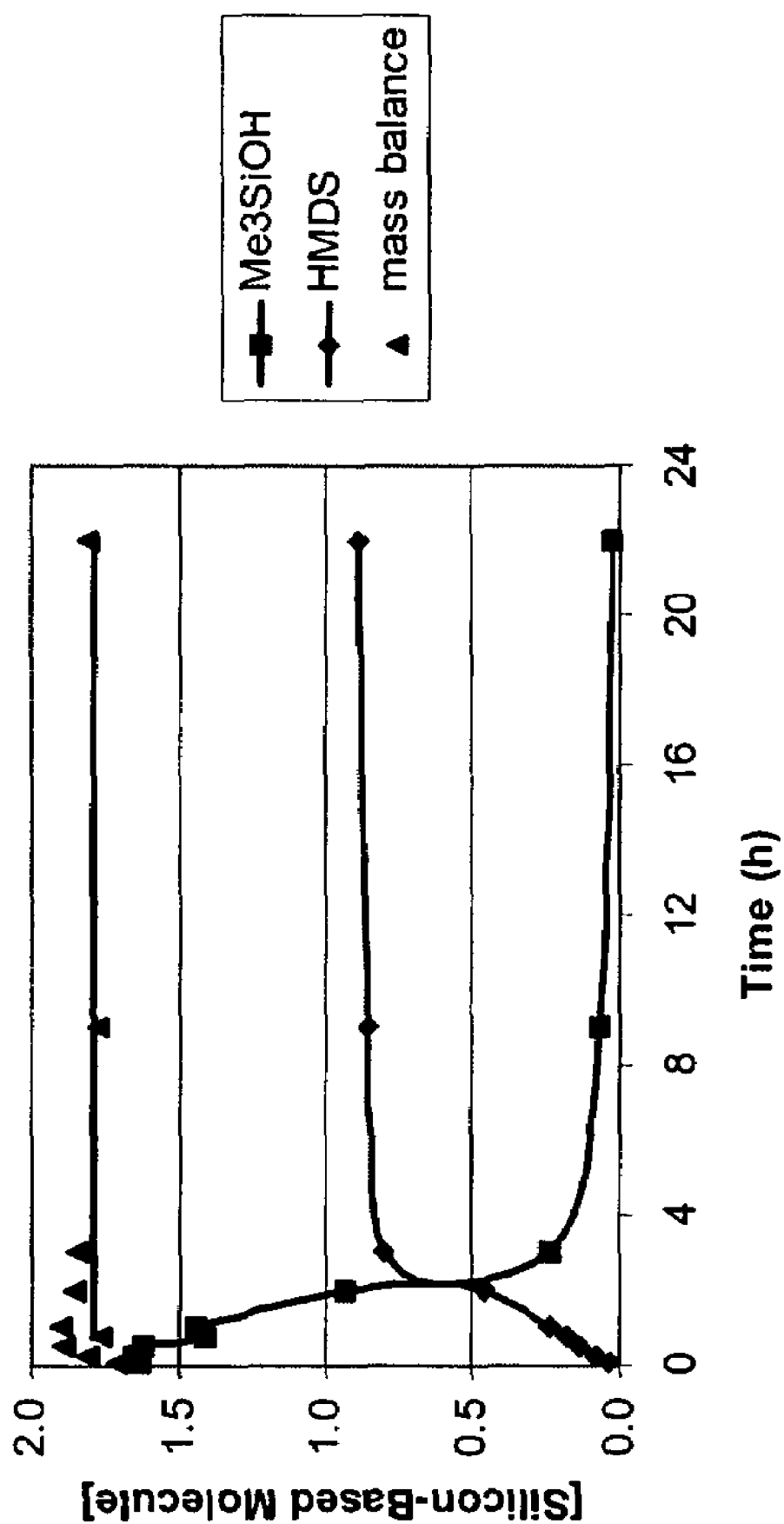
FIG. 10 illustrates trypsin-catalyzed condensation of trimethylsilanol at 25° C.

The trypsin-catalyzed condensation of trimethylsilanol was studied over a 24-hour period at 25° C. Independent reactions were formulated with a 4:1 monomer to enzyme weight ratio (~1000:1 silanol to trypsin mole ratio) in a neutral medium (pH 7.0) and performed for defined periods of time over 24 hours. The trypsin-catalyzed condensation of trimethylsilanol was nearly complete after three hours at 25° C. Based on the stoichiometry of the condensation reaction, two moles of trimethylsilanol were consumed for each mole of hexamethyldisiloxane (HMDS) produced (mass balance, FIG. 10). Conversely, the reversibility of the trypsin-catalyzed condensation reaction was studied with hexamethyldisiloxane in a neutral medium (pH 7.0) as well as an organic solvent (toluene). Since trimethylsilanol was not observed in the chromatographic results, trypsin was not observed to catalyze the hydrolysis of a siloxane bond in either medium. Although trypsin would theoretically catalyze the hydrolysis of a siloxane bond due to the law of microscopic reversibility, the reverse reaction was not favored under these conditions.

Based on the estimated solubility of trimethylsilanol in water (42.56 mg/mL), the concentration of trimethylsilanol (~160 mg/mL) saturated the aqueous medium and created a two-phase reaction mixture. Since proteases will only interact with water-soluble substrates, the trypsin-catalyzed condensation of trimethylsilanol was postulated to occur in the aqueous phase. Although the condensation reaction was conducted in water, the enzyme-catalyzed reaction was promoted by the phase separation of the product. The immiscibility of the product, hexamethyldisiloxane, changed the equilibrium and promoted the condensation reaction in the presence of water. Since the aqueous medium was saturated with trimethylsilanol, the reactant would continue to enter the aqueous phase due to the dynamic equilibrium of the condensation reaction. In addition, the hydrolysis or reverse reaction would be severely hindered due to the immiscibility of the disiloxane product in the aqueous phase.

Rate of Condensation During Time Example

The rate of condensation during the time study was analyzed, in order to begin to study the kinetics of the reaction catalyzed by trypsin at 25° C. Based on the time-independent stoichiometry of the proposed reaction, the rate (V) of condensation (Equation 1) and theoretical rate (Equation 2) equations were defined.

$$V=-0.5*(\delta[Me_3SiOH]/\delta t)=1*(\delta[HMDS]/\delta t) \quad \text{(Equation 1)}$$

$$V=k_R[Me_3SiOH]^\alpha[trypsin]^\beta \quad \text{(Equation 2)}$$

In Equation 1, the rate of condensation was defined as the change in concentration (i.e. [Molarity]=moles/L) of the reactant or product with time (e.g. $\delta[HMDS]/\delta t$). In Equation 2, the experimental rate constant ($k_R$) and the partial orders of reaction (i.e. $\alpha$ and $\beta$) with respect to each reactant were defined. The overall order of reaction is the sum of the partial orders (i.e. $\alpha+\beta$). Since trypsin was not consumed during the condensation reaction (i.e. a catalyst), the term was included in the rate constant ($k_R'$) and the theoretical rate equation (Equation 2) was simplified as defined in Equation 3. The general rate equation is depicted as Equation 4.

$$V=k_R'[Me_3SiOH]^\alpha, k_R'=k_R[trypsin]^\beta \quad \text{(Equation 3)}$$

$$V=-0.5*(\delta[Me_3SiOH]/\delta t)=k_R'[Me_3SiOH]^\alpha, \alpha=1 \text{ or } 2 \quad \text{(Equation 4)}$$

Since the solution is saturated with trimethylsilanol during most of the condensation reaction, the absolute amount of trimethylsilanol may be effectively constant. Given constant concentrations of trimethylsilanol and trypsin (i.e. catalyst), these reaction conditions would lead to a zero-order theoretical rate equation (Equation 2). In other words, the rate of condensation would be approximately constant. Since the initial (<3 hours) and final (>3 hours) rates of condensation or formation of HMDS are constant or linear, the data set appears to support this assessment. Based on the concentration of trypsin (i.e. $[E_t]$=[trypsin]=1.7 mM) and the rate of condensation (i.e. $V=-\delta[Me_3SiOH]/\delta t$=0.0064 M/m~2$\delta$ [HMDS]/$\delta t$ =0.0072 M/m), a relative value the turnover number ($k_{cat}$) or number of substrate molecules converted into product by an enzyme molecule in a unit time when the enzyme is fully saturated with substrate was calculated to be 4.0 reactions per minute ($m^{-1}$) or 0.066 reactions per second ($s^{-1}$) at 25° C.

Since trypsin may not be saturated due to the limited solubility of trimethylsilanol in water, the turnover number was treated as a relative value. Given a relative turnover number equal to 0.066 $s^{-1}$, the time period between each condensation reaction catalyzed by trypsin was calculated to be 15 s. In comparison to the maximum turnover numbers of other enzymes with their physiological substrates, the turnover number of the trypsin-catalyzed condensation of trimethylsilanol at 25° C. was several orders of magnitude (i.e. ~10-10,000,000) slower than the cited values. For example, the turnover number of the trypsin-catalyzed condensation of trimethylsilanol was approximately 1500 times slower than a natural chymotrypsin-catalyzed hydrolysis reaction.

Example 6

Evaluation of the Monomer to Enzyme Mole Ratio

Figure 11:
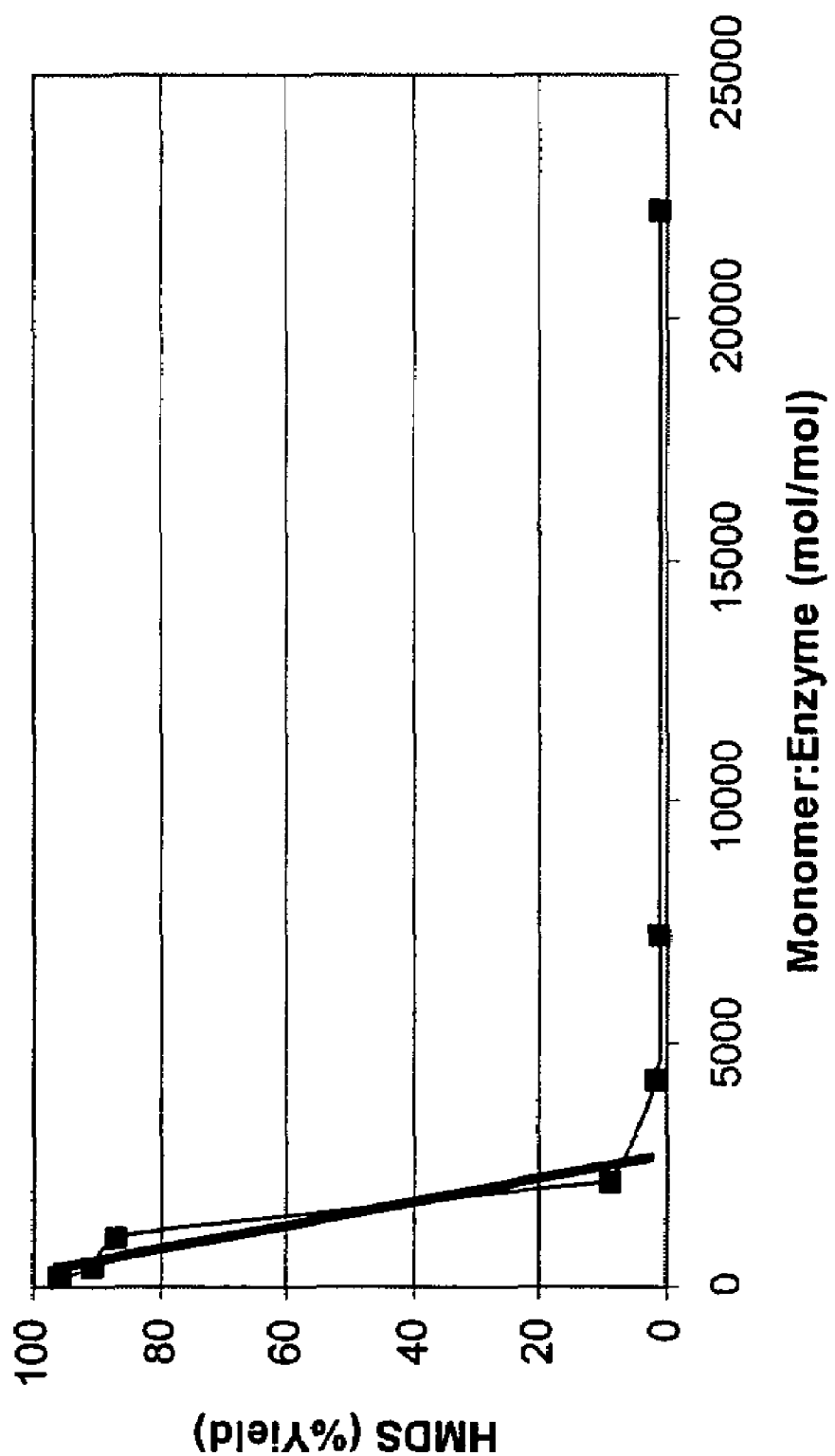
FIG. 11 illustrates saturated-trimethylsilanol to trypsin mole ratio study.

The rate of trimethylsilanol condensation was studied as a function of the monomer to enzyme mole ratio. The mole ratios were formulated with a constant amount of trimethylsilanol (160 mg/mL) and a variable amount of trypsin (2-198 mg/mL) in buffered water (pH 7.0). The closed (screw capped) reactions were conducted at 25° C. with magnetic stirring for three hours. The reaction products were isolated and quantitatively analyzed by GC (FIG. 11).

Figure 12:
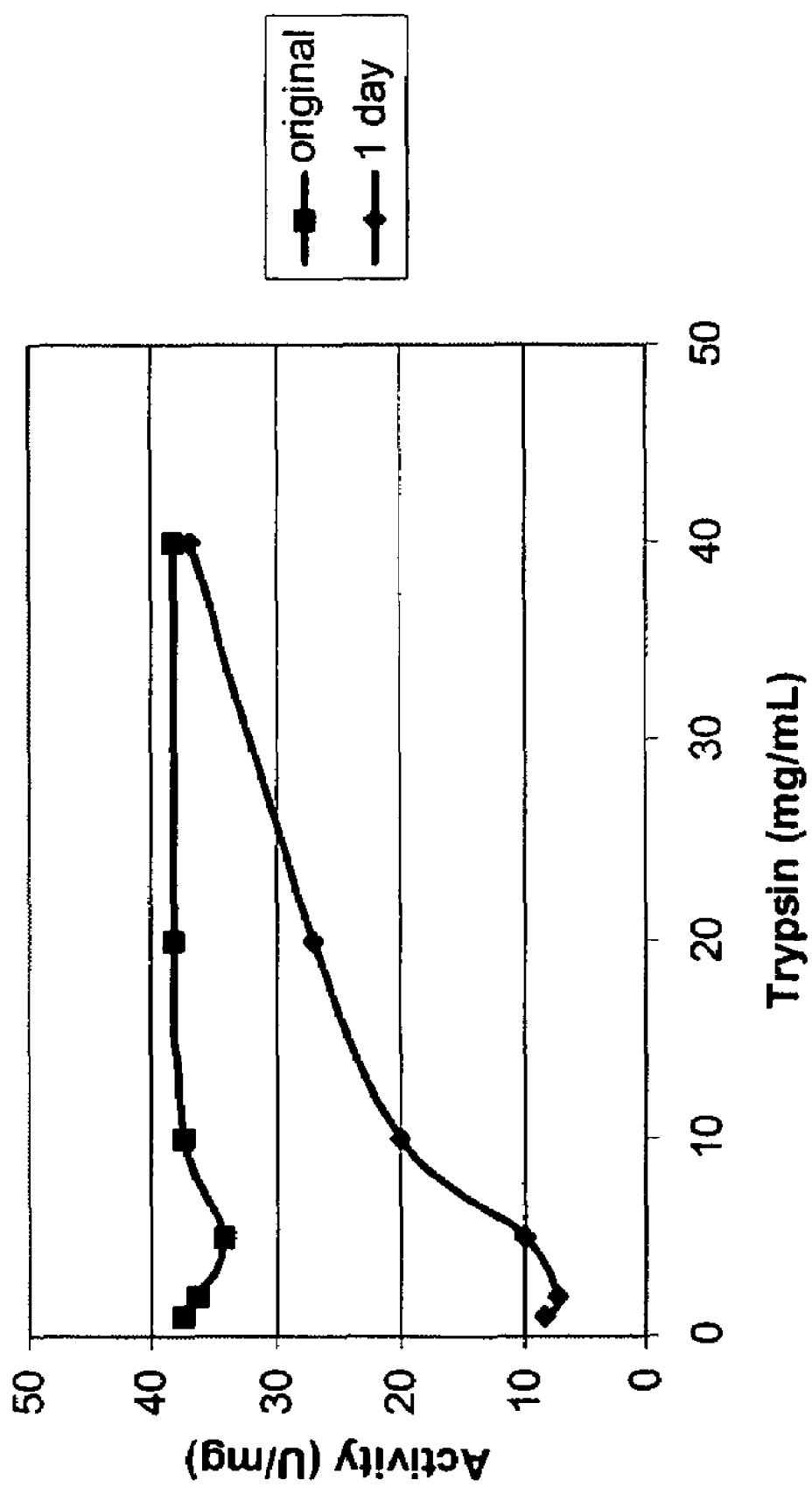
FIG. 12 illustrates the autolysis of trypsin at 25° C.

Based on the chromatographic results, the rate of reaction was determined to be dependent on the amount of trypsin. In addition, the interaction between these experimental variables was complicated due to the potential for autolysis at dilute concentrations of trypsin (i.e. <20 mg/ml). Given the decreased stability of dilute trypsin solutions (FIG. 12), a 1000:1 monomer to enzyme mole ratio was formulated in a 40-mg/mL solution of trypsin throughout the condensation study.

Since the reactions were conducted with a constant concentration of trimethylsilanol, a simplified theoretical rate equation (Equation 5) was used to perform a preliminary assessment of the partial-order of reaction with respect to trypsin. If the partial-order of reaction with respect to trypsin was first-order ($\beta$=1), the ratio of the rate of condensation (V) to the concentration of trypsin would be a constant value (Equation 6).

$$V=k_R'[trypsin]^\beta, k_R'=k_R[Me_3SiOH]^\alpha \quad \text{(Equation 5)}$$

$$k_R'=V/[trypsin]^1 \quad \text{(Equation 6)}$$

Since the condensation reactions were conducted for a fixed period of time (i.e. three hours), the amount of hexamethyldisiloxane (µmole) formed will be related to the rate of condensation (i.e. $V=[HMDS]_{3\ hours}$). A review of the chromatographic results showed that the calculated hexamethyldisiloxane to trypsin mole ratios were indeed approximately constant. In other words, the rate of condensation seemed to be directly proportional to the concentration of trypsin (theoretical black line, FIG. 11).

As observed, reducing the amount of trypsin by a factor of ten decreased the product yield by a factor of ten. This experimental observation supports the role of trypsin as a catalyst in the condensation of trimethylsilanol in a neutral medium and that it proceeds via a simple enzyme-substrate intermediate.

Example 7

Kinetic Study of the Trypsin-Catalyzed Condensation of Non-Saturated Solutions of Trimethylsilanol Since proteases only interact with water-soluble substrates, the concentration of trimethylsilanol was decreased (<42.56 mg/mL) to study the rate of condensation as a function of monomer concentration in a non-saturated medium. The amount of trimethylsilanol (~10-40 mg/mL, ~60-222 μmole) was adjusted to create homogeneous solutions in 40-mg/mL neutral (pH 7.0) solutions of trypsin. The reactions were conducted at 25° C. and 15° C. with magnetic stirring. After quenching the independent reactions, the reaction products were isolated and quantitatively analyzed by GC every 15 minutes over one-hour periods.

A differential method was used to determine the partial order of reaction with respect to trimethylsilanol. The logarithm of the theoretical rate equation (Equation 3) was calculated to yield a linear equation (Equation 7) in which the slope (α) was equal to the partial order of reaction with respect to trimethylsilanol.

$$\text{Log}(V) = \alpha \text{Log}[\text{Me}_3\text{SiOH}] + \text{Log}(k_R') \quad \text{(Equation 7)}$$

After plotting Log(V) vs. Log [Me$_3$SiOH] at 25° C. (α=0.9) and 15° C. (α=1.0), the partial order of reaction with respect to trimethylsilanol was estimated to be first-order. The plots of the differential rate equations with respect to trimethylsilanol were linear. The correlation coefficient ($R^2$) values were 94% and 98%, respectively. Since the rate of reaction was determined to be linearly dependent on the soluble amount of trimethylsilanol in the 40-mg/mL neutral (pH 7.0) solutions of trypsin, the reactions seem to be first-order with respect to trimethylsilanol. As hypothesized, the rate of condensation appears to be proportional to both the concentration of trimethylsilanol and trypsin.

Furthermore, the Lineweaver-Burk equation was used to study the ability of the trypsin-catalyzed condensation of trimethylsilanol to fit the Michaelis-Menten kinetic model. The chromatographic data sets acquired during the time studies at 25° C. and 15° C. yielded linear Lineweaver-Burk plots. Based on the linear equations of the experimental Lineweaver-Burk plots, the relative Michaelis constant ($K_m$) and maximum rate ($V_{max}$) values were calculated (Table 4).

TABLE 4

Relative Michaelis-Menten kinetic values.

| Trypsin-catalyzed condensation reaction | $K_m$ (μM) | $V_{max}$ (Mm$^{-1}$) |
|---|---|---|
| 25° C. | 6,000,000 | 0.05 |
| 15° C. | 17,000,000 | 0.10 |

Although the Michaelis-Menten kinetic values are relative, the large $K_m$ values indicate that the binding strength of the enzyme-substrate intermediate is weak. Comparatively, these $K_m$ values are several orders of magnitude (i.e. ~1,000-25,000,000) larger than the $K_m$ values of other enzymes. For example, the relative $K_m$ value of the trypsin-catalyzed condensation of trimethylsilanol at 25° C. was approximately 1200 times larger than the chymotrypsin-catalyzed hydrolysis of acetyl-L-tryptophanamide.

Since the relative $K_m$ values are large and the $V_{max}$ values are slow, the formation of the trypsin-silanol intermediate appears to be the rate-limiting step in the condensation reaction. This is consistent with the fact that trypsin was not saturated with trimethylsilanol in aqueous media. Therefore, the rate of condensation or hydrolysis of the trypsin-silanol intermediate must be faster than the formation of the enzymatic intermediate.

Figure 13:
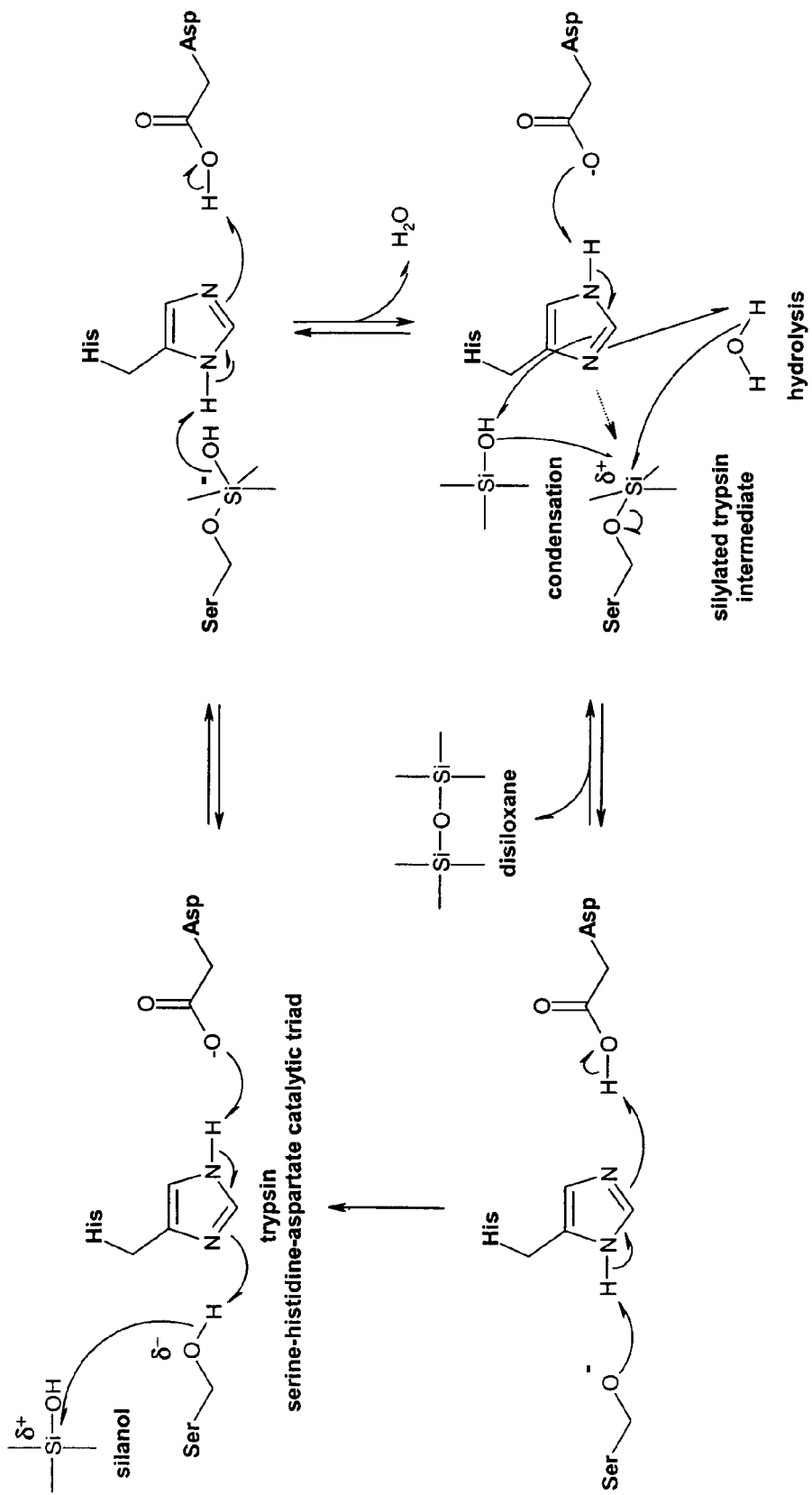
FIG. 13 illustrates the proposed reaction mechanism of trypsin-catalyzed condensation of trimethylsilanol.

Based on the stoichiometry of the silanol condensation reaction and the rate of condensation, the trypsin-catalyzed condensation of trimethylsilanol was hypothesized to have a reaction mechanism (FIG. 13) similar to the proteolytic hydrolysis of amide and ester bonds. Activated and stabilized by the charge-relay system of the catalytic triad, the nucleophilic oxygen atom of serine was postulated to attack the electropositive silicon atom of trimethylsilanol. Equivalent to the acyl-enzyme complex, a silylated trypsin intermediate would form followed by the loss of water. In addition, the nitrogen atom of the histidine could form a stabilized pentacoordinate species with the silicon atom in the intermediate. Based on the rate equation as well as the large relative $K_m$ and slow $V_{max}$ values, the formation of the trypsin-silanol intermediate appears to be the rate-limiting step. This is consistent with the fact that organosilicon molecules are larger than analogous hydrocarbon tryptic substrates. Subsequently, the silylated trypsin intermediate may participate in either a condensation or hydrolysis reaction with trimethylsilanol or water leading to the formation of the hexamethyldisiloxane (product) or trimethylsilanol (reactant), respectively. Since trypsin was not saturated with trimethylsilanol in aqueous media, the rate of condensation or hydrolysis of the trypsin-silanol intermediate must be faster than the formation of the enzymatic intermediate. Regardless, trypsin would be, recovered at the completion of either reaction.

Example 8

Trypsin pH Study

Figure 14:
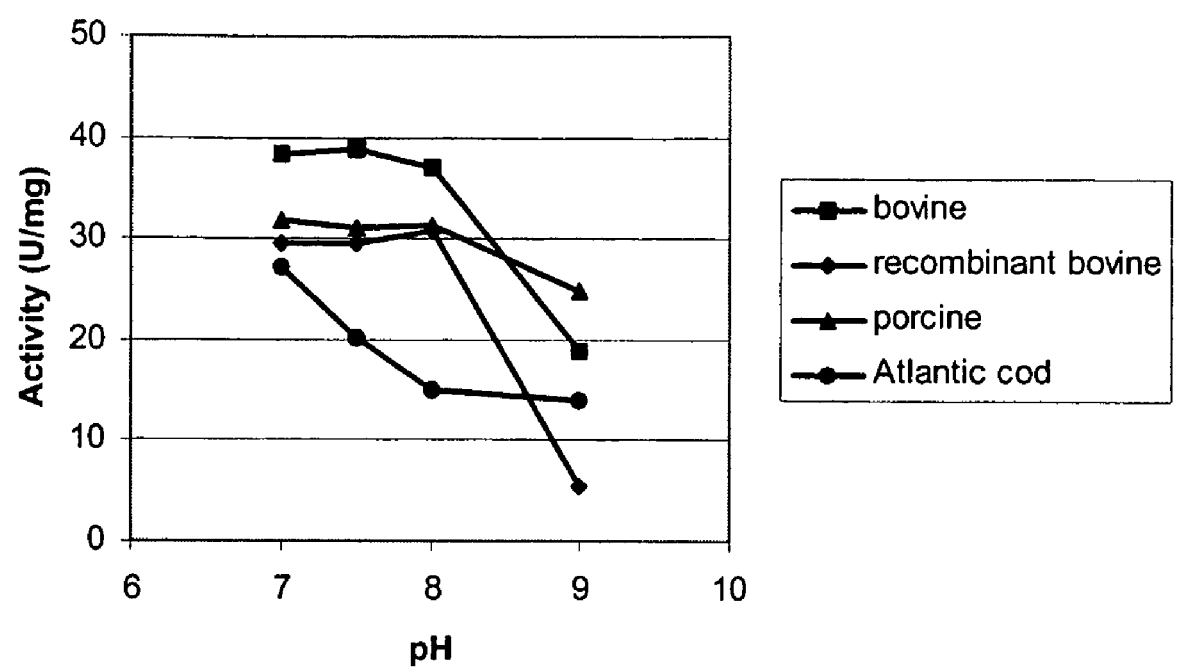
FIG. 14 illustrates a pH study of the activity of different tryptic species.

In nature, the optimum pH for trypsin-catalyzed hydrolysis is approximately 8. However, this is species dependent. As measured with a natural substrate (BAEE), the activities of different sources of trypsin were studied as a function of pH (FIG. 14).

Based on the spectrophotometric data, the profiles of the mammalian tryptic activities including the recombinant enzyme as a function of pH were similar. The mammalian source of bovine trypsin was observed to have the highest activity at pH 7.0. In comparison, the optimum pH of *Gadus morhua* (i.e. Atlantic cod) trypsin appeared to be more acidic. Since calcium was required to achieve the maximum activity and stability of trypsin, the differences in the relative activities may be due to variable levels of calcium. Based on an inductively coupled plasma-atomic emission spectroscopic analysis, the amount of calcium present in the commercial sources of trypsin was shown to be very different.

Calcium activation of trypsin induces changes in the tertiary structure of the enzyme. Specifically, calcium creates a compact structure due to increased helical content or an altered β-structure. The conformational changes have been hypothesized to be responsible for the documented increased enzymatic activity and thermal stability. Since the activity of trypsin is optimal in the presence of >10 mM (ideally, 20 mM or 400 ppm) calcium, the decreased levels of calcium in porcine pancreas and recombinant bovine trypsin correlate with their activities in comparison with bovine pancreatic trypsin.

Figure 15:
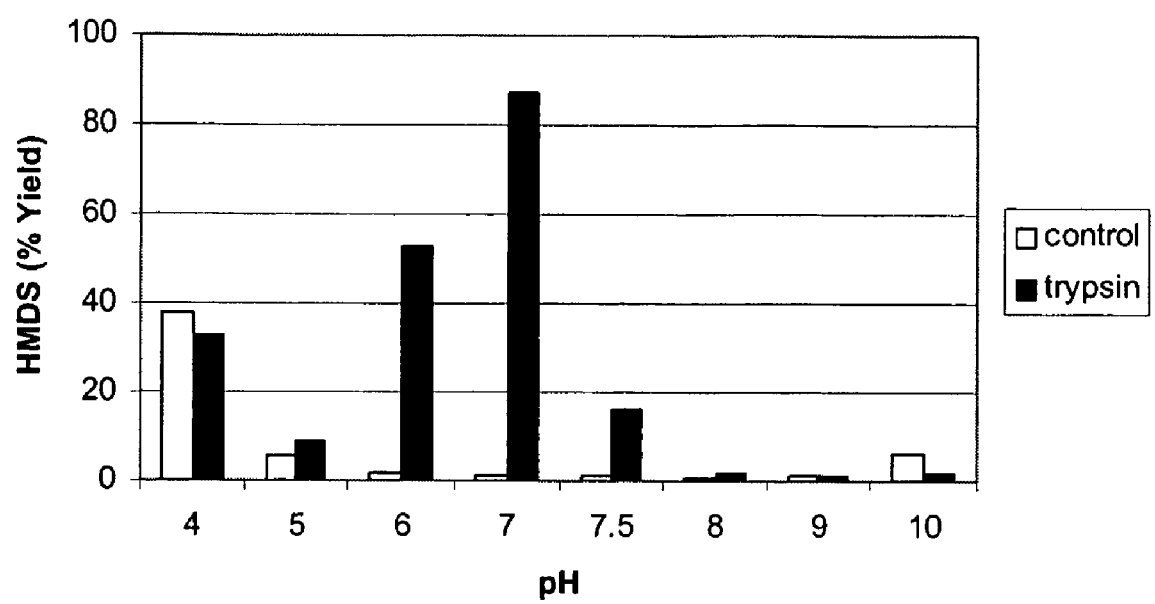
FIG. 15 illustrates the effect of pH on the trypsin-catalyzed condensation of trimethylsilanol.

Subsequently, the ability of bovine pancreatic trypsin to catalyze the trimethylsilanol condensation reaction was studied as a function of pH. The reactions were formulated with a 4:1 monomer to enzyme weight ratio (~1000:1 silanol to trypsin mole ratio) in aqueous media buffered from pH 4.0 to pH 10.0 and conducted at 25° C. for three hours. The reaction products were isolated and quantitatively analyzed by GC (FIG. 15). Based on the chromatographic data, the enzyme-catalyzed condensation reaction was dependent on the pH. The silanol condensation reaction was optimum at pH 7.0. Comparatively, acid- and base-catalyzed silanol condensation was observed in the negative control reactions; primarily, at pH values less than 4 and greater than 10 (FIG. 15).

Figure 16:
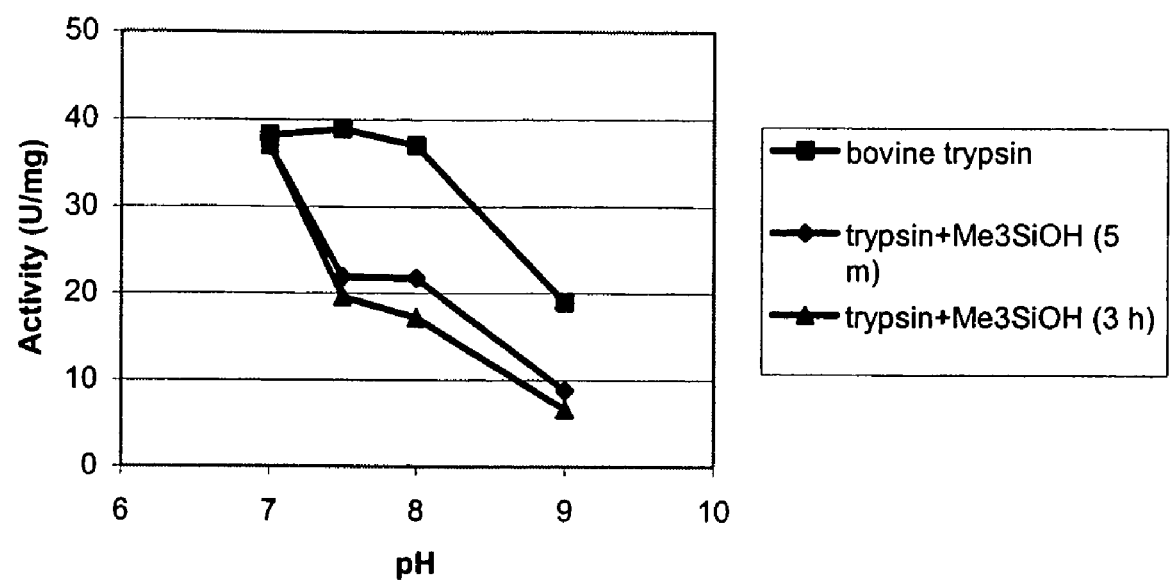
FIG. 16 illustrates the effect of trimethylsilanol and pH on trypsin activity.

Given the natural hydrolytic activity profiles measured with BAEE (FIG. 14), which show activity above pH 7, the decreased yields at pH values >7.0 were further investigated. As measured by the rate of hydrolysis of BAEE, the activities of bovine pancreatic trypsin were analyzed at the beginning (t=5 minutes) and end (t=3 hours) of condensation reactions conducted with trimethylsilanol in aqueous media buffered from pH 7.0 to pH 9.0. The spectrophotometric activity data is illustrated in FIG. 16.

In comparison to the natural pH activity profile (bovine trypsin, FIG. 16), trimethylsilanol partially inhibited (>50%) trypsin nearly immediately in basic buffered water (pH 7.5 to pH 9.0). Although trimethylsilanol did not inhibit trypsin in a neutral medium (pH 7.0), reactant inhibition increased by 50-65% with the basicity of the aqueous solution. Since trypsin was not denatured in the presence of trimethylsilanol, the inhibition of the hydrolysis (BAEE, FIG. 16) and condensation (trimethylsilanol, FIG. 15) reactions in basic media was hypothesized to be due to the silylation of other hydroxy-functional residues in the catalytic region. This would directly or indirectly reduce access to the active site and the activity of trypsin. As the pH decreases, these species would be prone to hydrolysis (acid catalysis), which would enable the active site to participate in the catalytic function of trypsin. Conversely, at high pH values, the longer lifetime of the silylated enzyme would inhibit both the hydrolysis of BAEE and the condensation of trimethylsilanol. These results further support the role of the active site of trypsin as a catalyst in the in vitro condensation of trimethylsilanol.

Example 9

Trypsin-Catalyzed Hydrolysis and Condensation of Trimethylethoxysilane

The role of trypsin in the formation of molecules with a single siloxane bond was studied during the in vitro hydrolysis and condensation of a model alkoxysilane, trimethylethoxysilane.

Prior to reaction, the alkoxysilane was pre-treated with sodium hydrogencarbonate due to the potential presence of residual chloro-functional silanes. The reactions were formulated with a 4:1 trimethylethoxysilane to protein weight ratio (~1000:1 alkoxysilane to trypsin mole ratio) in neutral media (pH 7.0) and conducted at 25° C. for three hours. Based on the estimated solubility of trimethylethoxysilane in water (1 mg/mL), the concentration of trimethylethoxysilane (~160 mg/mL) saturated the aqueous media and created two-phase reaction mixtures. The reaction products were isolated and quantitatively analyzed by GC (FIG. 17).

Although various rates of hydrolysis were observed, substantial condensation of trimethylethoxysilane was not observed in the negative control, non-specific protein (i.e. BSA, γ-globulins), small molecule (i.e. CaCl$_2$, imidazole, N-methylimidazole), and polypeptide (i.e. poly-L-lysine) reactions in comparison to the raw material. Although BSA and poly-L-lysine were not observed to catalyze the condensation of tetraethoxysilane or trimethylethoxysilane (FIG. 17), BSA and poly-L-lysine promoted the hydrolysis of trimethylethoxysilane and formation of trimethylsilanol at different rates in a neutral medium (pH 7.0).

Figure 17:
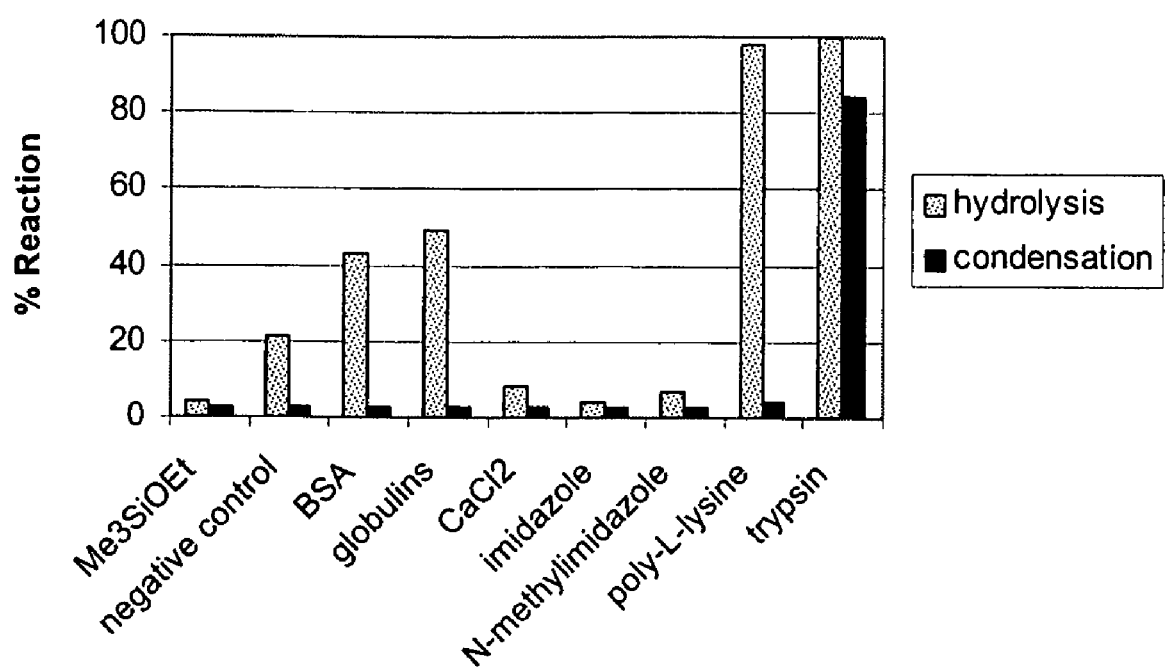
FIG. 17 illustrates the hydrolysis and condensation control reactions after three hours.

In the presence of trypsin, trimethylethoxysilane was hydrolysed (100%) and condensed (84%) during the formation of hexamethyldisiloxane in a neutral medium (pH 7.0) at 25° C. over three hours (FIG. 17). Since the relative rate of condensation decreased at temperatures <25° C. (FIG. 8), a time study of the trimethylethoxysilane reaction was conducted at 10° C. for defined periods of time over three hours. The reaction products were isolated and quantitatively analyzed by GC (FIG. 18).

Figure 18:
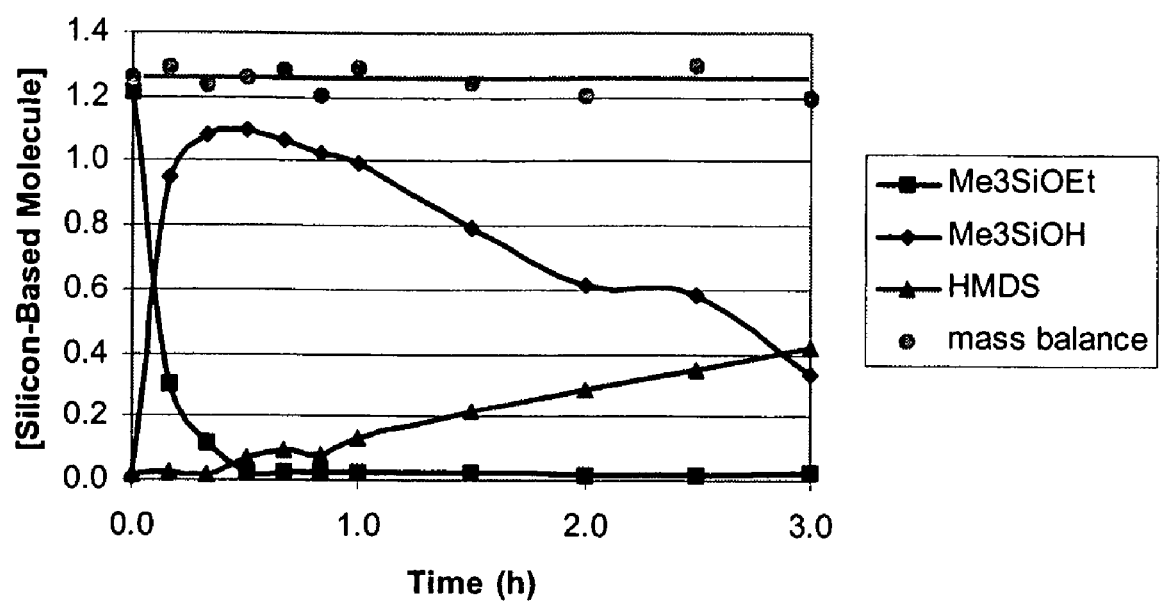
FIG. 18 illustrates trypsin-catalyzed hydrolysis and condensation of trimethylethoxysilane at 10° C.

Based on the stoichiometry of the hydrolysis and condensation reactions, two moles of trimethylethoxysilane were consumed in the formation of two moles of trimethylsilanol, which produced one mole of hexamethyldisiloxane (mass balance, FIG. 18). The chromatographic data set acquired during the time study was analyzed in order to study the kinetics of the hydrolysis and condensation reactions catalyzed by trypsin at 10° C. Comparatively, trimethylethoxysilane was readily hydrolysed within the initial 30 minutes and, subsequently, condensed during the formation of hexamethyldisiloxane.

The partial orders of the reactions with respect to reactants as well as the turnover numbers ($k_{cat}$) in the hydrolysis and condensation reactions were calculated. Since trypsin may not be saturated due to the limited solubility of trimethylethoxysilane in water, the turnover number was treated as a relative value. Given a relative turnover number equal to 0.53 s$^{-1}$, the time between each hydrolysis reaction catalyzed by trypsin was calculated to be approximately 2 s or 30 reactions per minute at 10° C. Although this is comparable with the maximum turnover number of lysozyme, the turnover number of the trypsin-catalyzed hydrolysis of trimethylethoxysilane at 10° C. was approximately 200 times slower than a chymotrypsin-catalyzed hydrolysis reaction. Given a relative turnover number equal to 0.048 s$^{-1}$, the time period between a condensation reaction catalyzed by trypsin was calculated to be approximately 20 s or 3 reactions per minute at 10° C.

Figure 19:
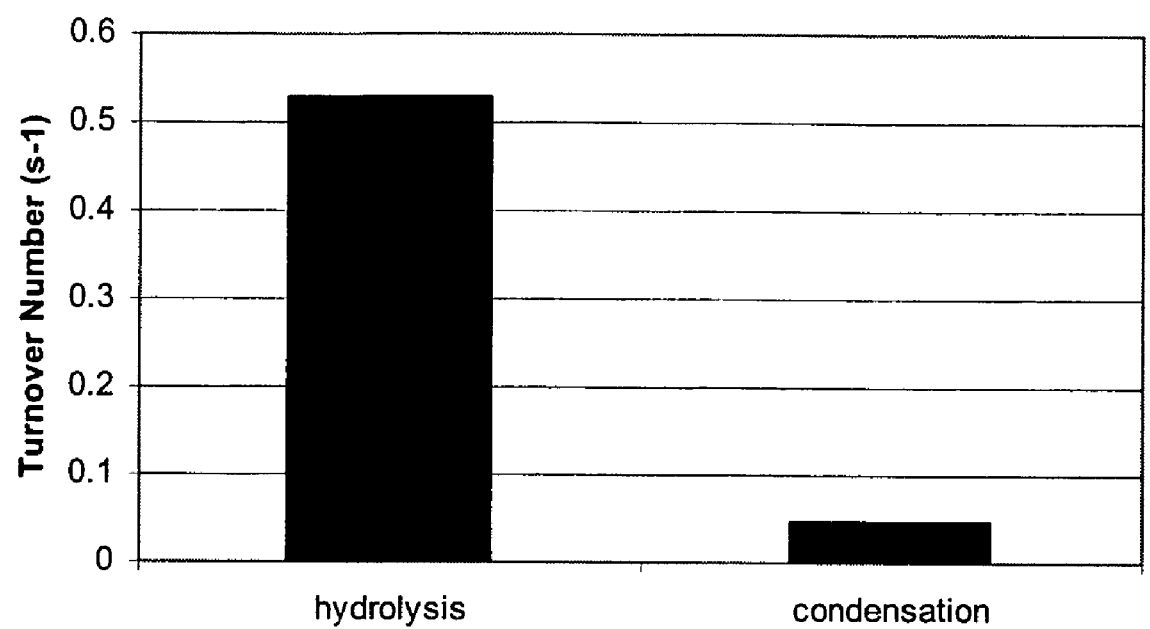
FIG. 19 illustrates turnover numbers of the trypsin-catalyzed hydrolysis of trimethylethoxysilane and condensation of trimethylsilanol at 10° C.

Based on the relative turnover numbers, the rate of the trypsin-catalyzed hydrolysis of trimethylethoxysilane (0.53 s$^{-1}$) was one order of magnitude (ten times) faster than the condensation of trimethylsilanol (0.048 s$^{-1}$) at 10° C. (FIG. 19). Comparatively, the rate of the trypsin-catalyzed condensation of trimethylsilanol ($k_{cat}$=0.066s$^{-1}$) at 25° C. was approximately 38% faster than the reaction conducted at 10° C.

Example 10

Alkoxysilane Study

Since trypsin catalyzed the formation of siloxane bonds, alternate mono-functional alkoxysilanes were chosen as substrates to investigate the ability of trypsin to selectively catalyze the in vitro hydrolysis and condensation of organo-functional alkoxysilanes under mild conditions. Initially, two additional trimethylalkoxysilanes were selected with comparatively polar (i.e. tetraethylene glycol monomethyl ether) and non-polar (i.e. hexanol) leaving groups to study the activity of trypsin as a function of the solubility of the reactant in a neutral medium (pH 7.0).

Figure 20:
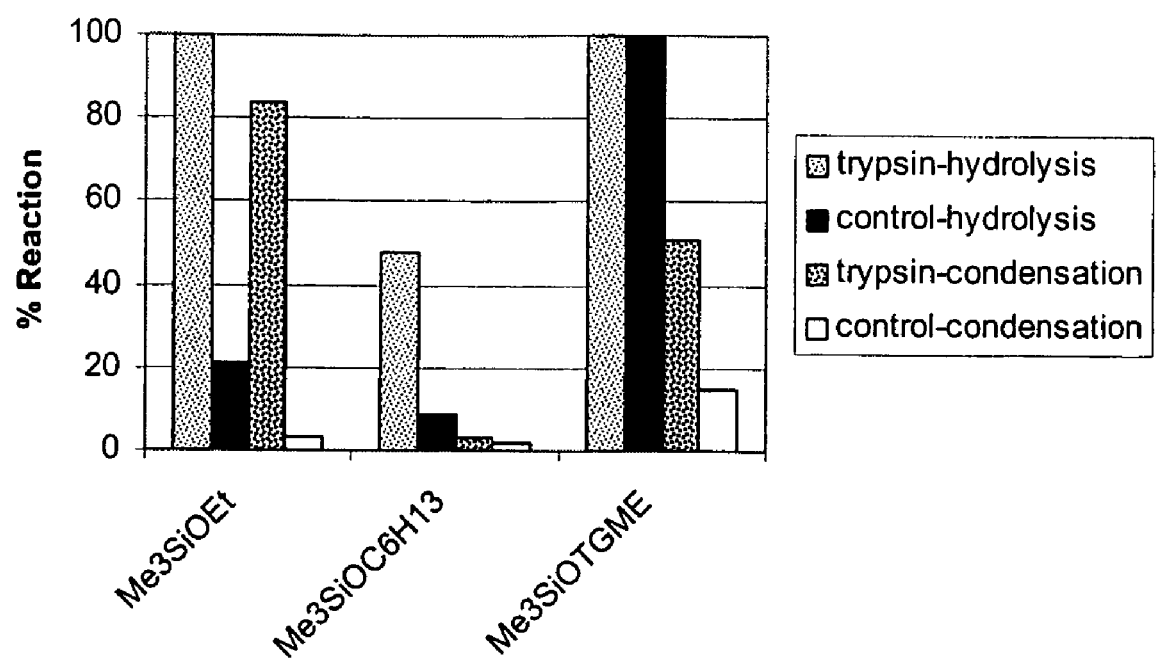
FIG. 20 illustrates trypsin-catalyzed hydrolysis and condensation of trimethylalkoxysilanes.

The two-phase reactions were formulated with a 4:1 monomer to enzyme weight ratio (>400:1 alkoxysilane to trypsin mole ratio) and conducted at 25° C. for three hours. The reaction products were isolated and quantitatively analyzed by GC (FIG. 20). Comparatively, the glycol-functional silane appeared to be more miscible than trimethylhexoxysilane in water. Based on the chromatographic results, trypsin catalyzed the partial hydrolysis of trimethylhexoxysilane without condensation. Although the role of trypsin in the hydrolysis of the glycol-functional silane was not definitive, trypsin catalyzed the condensation of the product, trimethylsilanol. The relative rates of the different hydrolysis and condensation reactions during the three-hour reactions were unknown.

Subsequently, four organo-functional alkoxysilanes were selected to study how the activity of trypsin varied as a result of different steric and electronic interactions with the substrate. The four organo-functional alkoxysilanes are phenyldimethylethoxysilane (PhMe$_2$SiOEt), triphenylethoxysilane (Ph$_3$SiOEt), 3-glycidoxypropyldimethylethoxysilane ((epoxy)Me$_2$SiOEt), and aminopropyldimethylethoxysilane ((H$_2$N(CH$_2$)$_3$)Me$_2$SiOEt).

Figure 21:
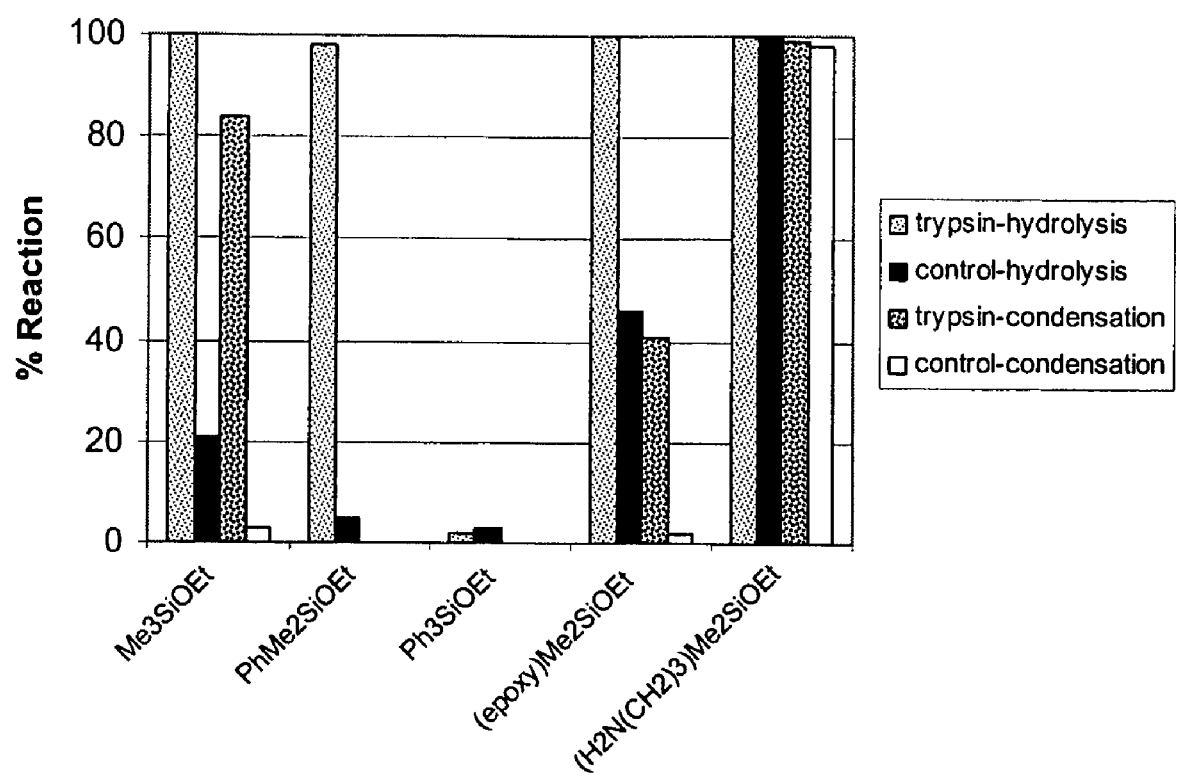
FIG. 21 illustrates trypsin-catalyzed hydrolysis and condensation of ethoxysilanes.

The two-phase reactions were formulated with a 4:1 monomer to enzyme weight ratio (>300:1 alkoxysilane to trypsin mole ratio) and conducted at 25° C. for three hours. The reaction products were isolated and quantitatively analyzed by GC (FIG. 21). Based on the chromatographic results, trypsin was observed to preferentially catalyze the hydrolysis and condensation of trimethylethoxysilane and 3-glycidoxypropyldimethylethoxysilane. Comparatively, phenyldimethylethoxysilane was hydrolysed but not condensed, while triphenylethoxysilane was neither hydrolysed nor condensed in the presence of trypsin. Given the documented traits of the binding domain within the catalytic region of trypsin, the decrease in enzymatic activity appeared to be due to the increased hydrophobicity and steric bulk of the phenyl-functional substrates. Despite trypsin's affinity for basic residues, aminopropyldimethylethoxysilane was fully hydrolysed and condensed in the presence and absence of trypsin. The basic amino-functional alkoxysilane catalyzed the formation of the disiloxane product, which was stabilised by an extra-coordinate intermediate with the primary amine.

Figure 22:
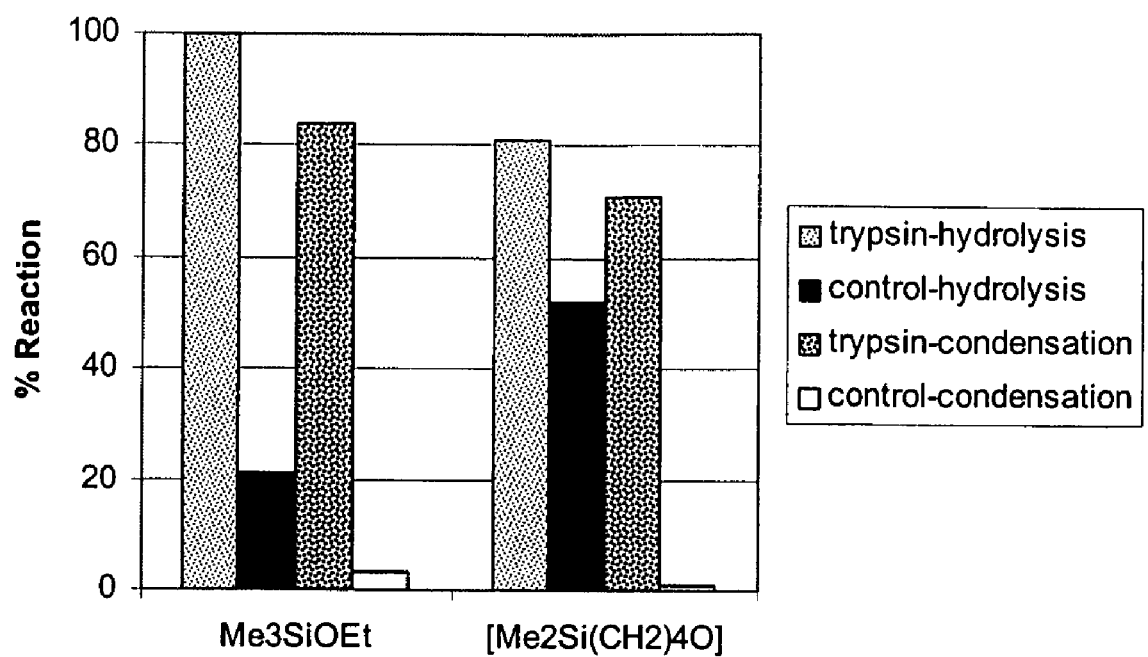
FIG. 22 illustrates trypsin-catalyzed hydrolysis and condensation of 1,1-dimethyl-1-sila-2-oxacyclohexane.

Alternatively, two silicon-functional molecules with cyclic architectures were chosen to further investigate the ability of trypsin to catalyze the cleavage and formation of Si—O bonds. The two-phase reactions were formulated with a 4:1 monomer to enzyme weight ratio and conducted at 25° C. for three hours (Schemes 2-3). The reaction products were isolated and quantitatively analyzed by GC (FIG. 22).

Scheme 2:
Trypsin-catalyzed hydrolysis and condensation of 1,1-dimethyl-1-sila-2-oxacyclohexane.

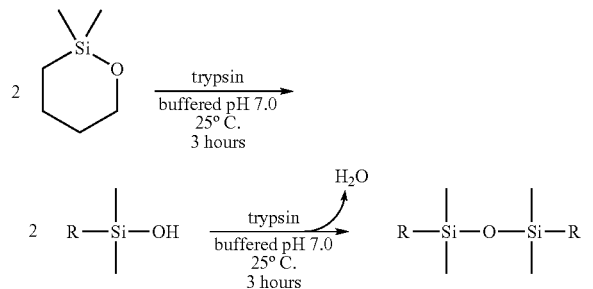

R = carbinol (i.e. (CH$_2$)$_4$OH).

Scheme 3:
Trypsin-catalyzed condensation of heptamethylhydroxytetracyclosiloxane.

Based on the chromatographic results, trypsin catalyzed the ring-opening hydrolysis of 1,1-dimethyl-1-sila-2-oxacyclohexane and condensation of hydroxybutyldimethylsilanol during the formation of the carbinol-functional disiloxane (Scheme 2). Trypsin did not catalyze the condensation of heptamethylhydroxytetracyclosiloxane. Despite their cyclic architectures, these organosilicon molecules and the resultant intermediates and products were different. Comparatively, the cyclic siloxane is sterically larger than the cyclic alkoxysilane. Analogous to basic residues (Scheme 4), the carbinol-functional silanol intermediate was hypothesized to be an acceptable substrate due to its ability to hydrogen bond with the aspartic acid residue within the binding domain of the catalytic region of trypsin.

Scheme 4:
Established (lysine and arginine and proposed (silanol) hydrogen-bonding within the binding domain of trypsin.

trypsin binding domain

In comparison to a control reaction, trypsin reportedly did not catalyze the polycondensation of a silicic acid precursor, tetraethoxysilane, in an aqueous medium at pH 6.8. In this study, no reaction products were observed in a replicate reaction formulated with a 4:1 monomer to enzyme weight ratio and conducted at 25° C. for three hours. Specifically, trypsin did not hydrolyze or condense tetraethoxysilane during the three-hour reaction. Comparatively, following a seven-day reaction, trypsin was observed to catalyze the polycondensation of tetraethoxysilane during the formation of a solid composite containing silica and trypsin. The role of the active site of trypsin in the polycondensation of tetraethoxysilane was not definitive in this study. In review, trypsin was observed to selectively catalyze the hydrolysis and condensation of organo-functional alkoxysilanes under mild conditions.

Example 11

Proteinaceous Inhibition Study

Figure 23:
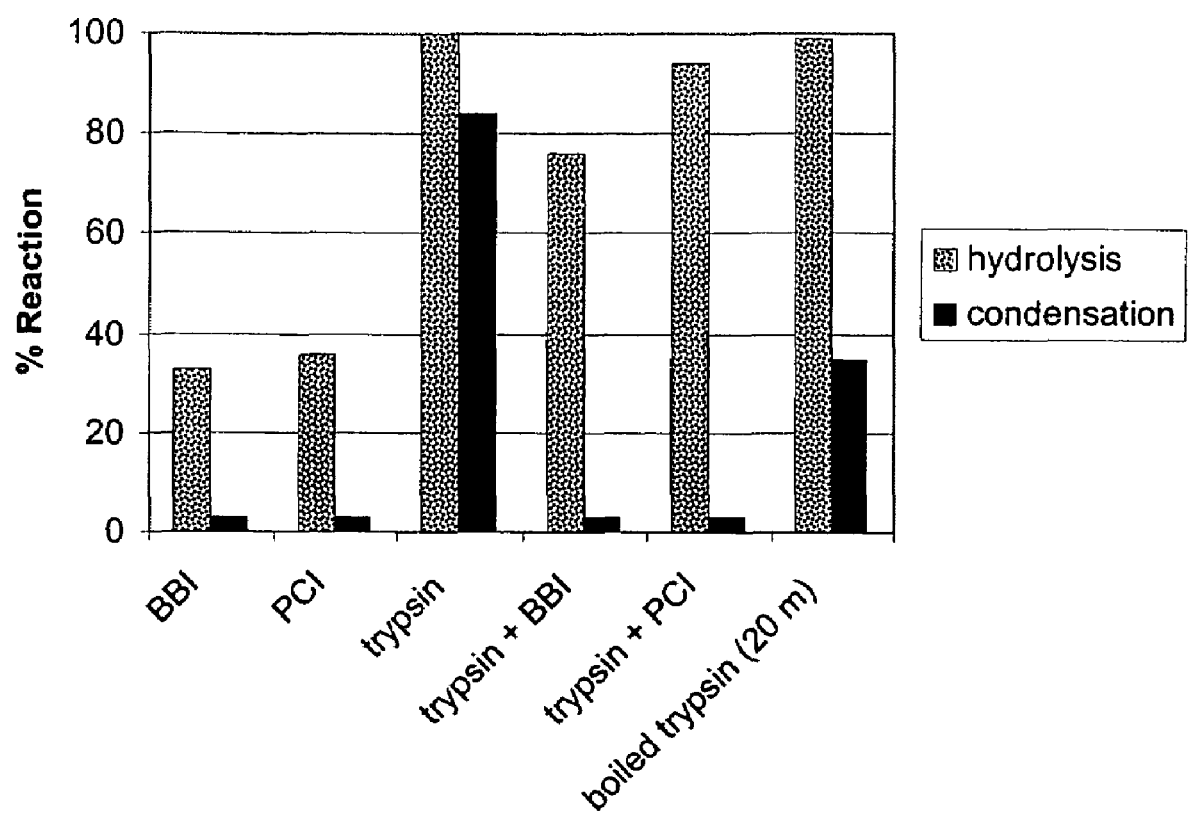
FIG. 23 illustrates proteinaceous inhibition of the trimethylethoxysilane reaction.

A proteinaceous inhibition study was conducted to investigate the role of the enzymatic active site in the hydrolysis and condensation of trimethylethoxysilane. Prior to reaction, trypsin was independently inhibited with an excess amount of the Bowman-Birk inhibitor (4:1 BBI to trypsin mole ratio) and the Popcorn inhibitor (2:1 PCI to trypsin mole ratio) in stirred neutral media (pH 7.0) for two hours. Based on standard enzymatic activity assays, trypsin was fully inhibited by the BBI (98%) and PCI (91%). The reactions were formulated with a 4:1 monomer to enzyme weight ratio (~1000:1 trimethylethoxysilane to trypsin mole ratio) and conducted at 25° C. for three hours. The reaction products were isolated and quantitatively analyzed by GC (FIG. 23).

Although the treated enzymes were observed to catalyze the hydrolysis of trimethylethoxysilane, the condensation of trimethylsilanol was completely inhibited in comparison to the control reactions. Notably, the percent hydrolysis decreased in the presence of the BBI- (24%) and PCI- (6%) inhibited trypsin. Following thermal denaturation, the activity of trypsin was comparable to the proteinaceous inhibition and previous denaturation experiments. Consequently, it appeared that non-specific interactions with trypsin, including the active site, promoted the hydrolysis of trimethylethoxysilane. However, the active site of trypsin was determined to selectively catalyze the in vitro condensation of trimethylsilanol under mild conditions.

Example 12

Figure 24:
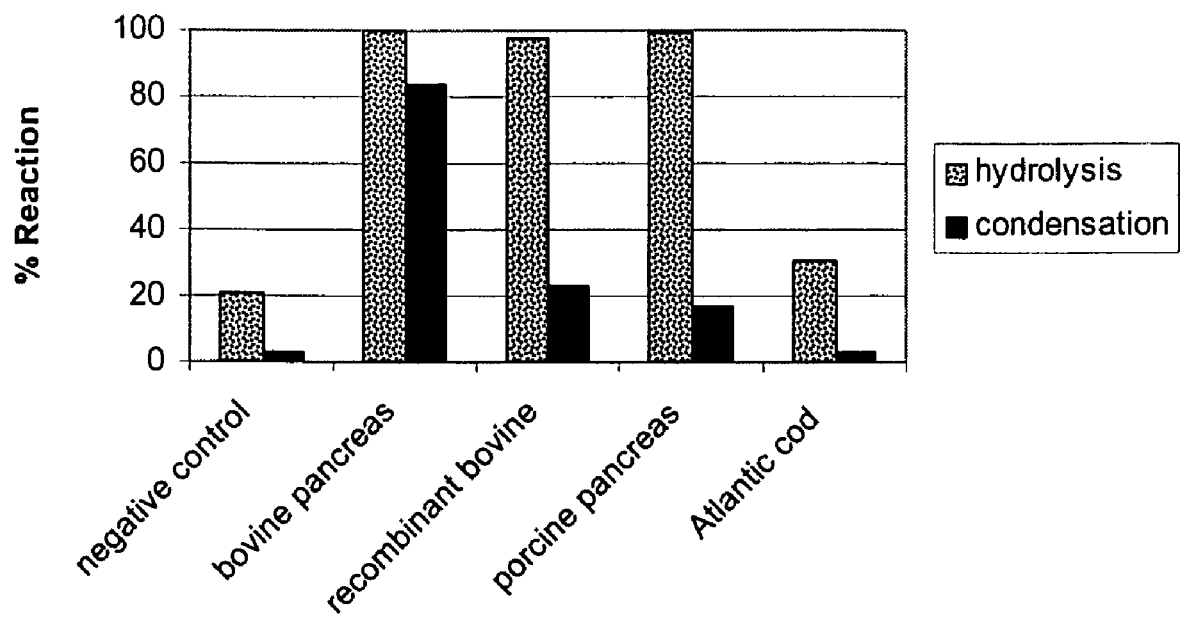
FIG. 24 illustrates the hydrolysis and condensation of trimethylethoxysilane by different sources of trypsin.

Hydrolysis and Condensation of Trimethylethoxysilane with Different Sources of Trypsin Although various sources (e.g. mammalian, fish) of trypsin are similar (e.g. tertiary structure), their selectivity and activity may be different. Consequently, the ability of porcine pancreas, *Gadus morhua* (i.e. Atlantic cod), and recombinant bovine trypsin to catalyse the hydrolysis of trimethylethoxysilane and condensation of trimethylsilanol was evaluated in neutral media (pH 7.0) at 25° C. Although the pH may not have been optimal for these different sources of trypsin, a neutral pH was used to minimise acid- and base-catalysed hydrolysis and condensation. The reaction products were isolated and quantitatively analysed by GC (FIG. 24).

Based on the chromatographic results, trypsin from porcine pancreas (i.e. mammalian) as opposed to Atlantic cod (i.e. fish) was observed to catalyse the hydrolysis and condensation reactions. Similar to the pH profiles measured with a natural substrate (FIG. 14), the activity of trypsin from bovine pancreas was greater than the alternate sources of trypsin including the recombinant enzyme in a neutral medium (pH 7.0). The inactivity of trypsin from the Atlantic cod appeared to be due to pH (FIG. 14). Since calcium was required to achieve the maximum activity and stability of trypsin, these observations may have been due to different optimum pH ranges and/or levels of calcium.

Figure 25:
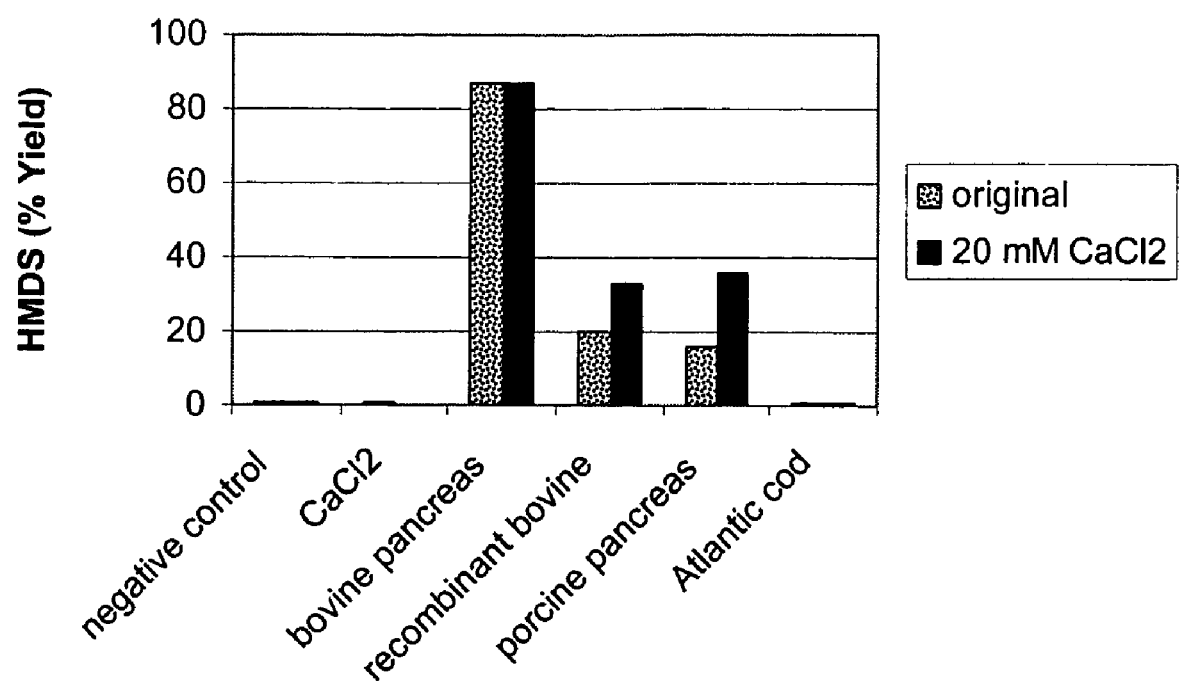
FIG. 25 illustrates the effect of calcium on the trypsin-catalyzed condensation of trimethylsilanol.

Calcium activation of trypsin induces changes in the tertiary structure of the enzyme. Since the activity of trypsin is optimal in the presence of >10 mM calcium, the ability of trypsin to catalyse the condensation of trimethylsilanol was studied in a neutral medium (pH 7.0) containing 20 mM $CaCl_2$. The reactions were formulated with a 4:1 monomer to enzyme weight ratio (~1000:1 silanol to trypsin mole ratio) and conducted at 25° C. for three hours. The reaction products were isolated and quantitatively analysed by GC (FIG. 25).

In comparison to the original sources of trypsin, the activities as measured by the yield of the recombinant bovine and porcine pancreas trypsin-catalysed reactions increased 65% and 125%, respectively. Comparatively, the yield of the bovine pancreas and Atlantic cod trypsin-catalysed reactions did not change. In the absence of calcium chloride (FIG. 24), porcine pancreas and recombinant bovine trypsin catalysed the complete hydrolysis of trimethylethoxysilane during the formation of trimethylsilanol. In the presence of calcium chloride, the increased activity of the porcine pancreas and recombinant bovine trypsin provided indirect evidence that the tertiary structure of the catalytic region was directly involved in the in vitro condensation of trimethylsilanol. Based on the yields of the hydrolysis and condensation reactions, the commercial source of bovine pancreatic trypsin (i.e. 886 ppm Ca) appeared to be optimal in a neutral medium (pH 7.0). Comparatively, the potential effect of 20 mM calcium chloride was negligible in the presence of 2.1% calcium in the commercial source of Atlantic cod trypsin. The substrate selectivity and activity of the tryptic sources appeared to be different despite similar tertiary structures.

Example 13

Enzyme-Catalyzed Polycondensation and Ring-Opening Polymerization of Silicon-Based Monomers The ability of trypsin to catalyze the formation of siloxane bonds during the in vitro polycondensation and ring opening polymerization of silicon-based monomers was explored under mild conditions.

Trypsin-Catalyzed Polycondensation of Methyltriethoxysilane

Given the catalytic role of trypsin in the model siloxane condensation reactions, trypsin was used as a catalyst in the polycondensation of a trifunctional alkoxysilane, methyltriethoxysilane, under mild conditions. The reaction was formulated with a 4:1 methyltriethoxysilane (0.091 g, 511 μmol, 3.25 mmol Si) to trypsin (0.022 g, 0.9 μmol) weight ratio (~550 monomer to enzyme mole ratio) in a neutral medium (pH 7.0) and conducted at 25° C. for seven days (Scheme 5).

Scheme 5:
Trypsin-catalyzed polycondensation of methyltriethoxysilane.

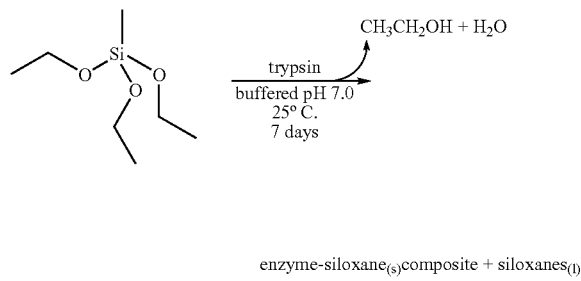

enzyme-siloxane$_{(s)}$composite + siloxanes$_{(l)}$

The solid and liquid reaction products were isolated and selectively characterized by infrared spectroscopy, microscopy, and mass spectrometry techniques.

Based on the diffuse reflectance infrared Fourier transform spectra of trypsin and the solid reaction product, the isolated solid was determined to be a composite material containing a mixture of methylsilsesquioxane resin and trypsin. Comparatively, the spectral peaks of a methylsilsesquioxane resin were observed in the presence of a control spectrum acquired with trypsin. Specifically, the symmetric methyl deformation (MeSiO$_{3/2}$, near 1270 cm$^{-1}$), siloxane asymmetric stretch (SiOSi, near 1000-1130 cm$^{-1}$), as well as the asymmetric methyl rock and silicon-carbon stretch (MeSiO$_{3/2}$, near 778 cm$^{-1}$) were observed in the presence of the spectral peaks associated with trypsin. The solid was observed to contain thick agglomerates ranging in size from approximately 200 μm to 1.5 mm. The rough surfaces of the agglomerate particles were composed of submicron round particles. Based on an energy dispersive spectroscopy (SEM-EDS) analysis, the surfaces of the particles were determined to contain silicon, oxygen, carbon, and sulfur. These elements are consistent with the functionality of methylsilsesquioxane and trypsin. The surface also contained sodium and chloride due to the use of a salt (NaCl) in the extraction procedure. Based on the silicon (Si) stoichiometry of the polycondensation reaction, the trypsin-catalyzed polycondensation reaction yielded 12% solid (0.011 g, 0.39 mmol Si). Comparatively, a solid precipitate was not observed in the negative control reaction.

The liquid reaction products were isolated and characterized by electrospray ionisation mass spectrometry (ESI MS). Although methyltriethoxysilane was not observed in the spectral results, substantial hydrolysis and condensation of methyltriethoxysilane was not observed in the absence of trypsin. Primarily, ethoxy-functional low molecular weight oligomers (e.g. dimers, trimers, tetramers) and cyclic siloxanes were observed in the ESI MS spectrum. In comparison to the negative control reaction, trypsin promoted the complete hydrolysis and, subsequent, polycondensation of methyltriethoxysilane. The distributions of linear, cyclic, and branched siloxane molecules were fully hydroxylated. Although trypsin promoted the hydrolysis of the alkoxy-functional silicones, the role of the active site of trypsin in the polycondensation of these molecules was not definitive in this study.

Although the ESI MS results are qualitative, the reaction products in the solid and liquid phases fully detail the polycondensation reactions. Prior to the precipitation of agglomerated silsesquioxanes in the presence of trypsin, the formation of linear, cyclic, and branched oligomers during the polycondensation of methyltriethoxysilane was analogous to the polymerization behavior of silica.

Trypsin-Catalyzed Ring-Opening Polymerization of Cyclic Siloxanes

The ability of trypsin to catalyze the cleavage and formation of Si—O bonds during the ring opening polymerization of cyclic siloxanes was explored under mild conditions. Specifically, five cyclic siloxanes: hexamethylcyclotrisiloxane, octamethylcyclotetrasiloxane, trimethyltri(trifluoropropyl)cyclotrisiloxane, tetramethyltetra(trifluoropropyl)cyclotetrasiloxane, and tetramethyltetraphenylcyclotetrasiloxane, were selected to study how the activity of trypsin varied as a result of different steric and electronic interactions with the substrate.

The two-phase reactions were formulated with a 4:1 monomer to enzyme weight ratio and conducted at 25° C. in neutral media (pH 7.0) for 8 days. The reaction products were isolated and qualitatively analyzed by GC (Table 5).

TABLE 5

Trypsin-catalyzed ring opening polymerization of cyclic siloxanes at 25° C.

| | Cyclic Area Percent[1] | | | | | |
|---|---|---|---|---|---|---|
| | Trimer (x = 3) | | Tetramer (x = 4) | | Pentamer (x = 5) | |
| Cyclic Siloxane | Control | Trypsin | Control | Trypsin | Control | Trypsin |
| A, [Me$_2$SiO]$_3$ | (100) | (100) | | | | |
| B, [Me$_2$SiO]$_4$ | (0.2) | (0.2) | (99.8) | (99.8) | | |
| C, [Me(CF$_3$CH$_2$CH$_2$)SiO]$_3$ | (97.5) | (97.1) | (1.7) | (1.9) | (0.8) | (1.0) |
| D, [Me(CF$_3$CH$_2$CH$_2$)SiO]$_4$ | (0.2) | (0) | (96.3) | (94.9) | (3.4) | (5.1) |
| E, [Me(Ph)SiO]$_4$ | | | (100) | (100) | | |

[1]The GC cyclic area percent values are qualitative.

Based on the chromatographic data, trypsin was not observed to catalyze the hydrolysis of the cyclic siloxane bonds. As previously reported, trypsin was unable to hydrolyze hexamethyldisiloxane in a neutral medium (pH 7.0) at 25° C. Since proteases will only interact with water-soluble substrates, the hydrolysis reactions would be severely hindered due to the immiscibility of the cyclic siloxanes in the aqueous phase. Although trypsin would theoretically catalyze of the hydrolysis of a siloxane bond due to the law of microscopic reversibility, the reverse reaction was not favored.

The invention claimed is:

1. A method of forming an organic molecule, comprising contacting a hydrolase enzyme with an organic reactant, wherein:
   the organic reactant is selected from the group consisting of:
   $(CH_3)_2Si(OCH_3)_2$; $(CH_3)(CF_3CH_2CH_2)Si(OCH_3)_2$; $(C_6H_5)(CH_3)Si(OCH_3)_2$; $(CH_3CH_2)_2Ge(OCH_2CH_3)_2$; $(CH_3)Si(OCH_2CH_3)_3$; 1,3,5,7-tetramethyl-1,3,5,7-tetramethoxy-cyclotetrasiloxane; 1,3-bis(hydroxy)tetramethyldisiloxane; $[(HO)_2(CH_3)SiO]_3SiCH_3$, $(Me_3SiO(CH_2CH_2O)_4CH_3)$, 3-glycidoxypropyldimethylethoxysilane, 1,1-dimethyl-1-sila-2-oxacyclohexane, trimethylsilanol, trimethylethoxysilane or a combination thereof;
   the hydrolase enzyme is selected from the group consisting of: *Candida antarctica* lipase, *Candida antarctica* lipase B, *Rhizomucor miehei* lipase, wheat germ lipase, trypsin, cutinase, or a combination thereof; and
   the hydrolase enzyme catalyzes the hydrolysis and condensation of the organic reactant to form the organic molecule.

2. The method according to claim 1, wherein the hydrolase enzyme is trypsin.

3. The method according to claim 1, wherein the concentration of hydrolase enzyme is equal to or greater than 1 mg/mL.

4. The method according to claim 3, wherein the concentration of hydrolase enzyme is from about 20 mg/mL to about 60 mg/mL.

5. The method according to claim 1, wherein the organic reactant to enzyme mole ratio is less than or equal to about 40000:1.

6. The method according to claim 1, wherein the reaction is conducted at a pH from about 5.0 to about 8.0.

7. The method according to claim 1, wherein the reaction is conducted in an aqueous solution, or a solvent.

8. The method according to claim 1, wherein the reaction is conducted at a temperature of between about 5° C. to about 90° C.

9. The method according to claim 8, wherein the reaction is conducted at a temperature of between about 20° C. to about 50° C.

10. The method according to claim 9, wherein the reaction is conducted at a temperature of about 25° C.

11. A method of forming an organic intermediate molecule, comprising contacting a hydrolase enzyme with an organic reactant, wherein:
    the organic reactant is selected from the group consisting of:
        $(CH_3)_2Si(OCH_3)_2$; $(CH_3)(CF_3CH_2CH_2)Si(OCH_3)_2$; $(C_6H_5)(CH_3)Si(OCH_3)_2$; $(CH_3CH_2)_2Ge(OCH_2CH_3)_2$; $(CH_3)Si(OCH_2CH_3)_3$; 1,3,5,7-tetramethyl-1,3,5,7-tetramethoxy-cyclotetrasiloxane; $(Me_3SiO(CH_2CH_2O)_4CH_3)$, 3-glycidoxypropyldimethylethoxysilane, 1,1-dimethyl-1-sila-2-oxacyclohexane, trimethylethoxysilane or a combination thereof,
    the hydrolase enzyme is selected from the group consisting of *Candida antarctica* lipase, *Candida antarctica* lipase B, *Rhizomucor miehei* lipase, wheat germ lipase, trypsin, cutinase, or a combination thereof; and
    the hydrolase enzyme catalyzes the hydrolysis of the organic reactant to form the organic intermediate molecule.

12. A method of forming an organic molecule, comprising contacting a hydrolase enzyme with an organic intermediate reactant, wherein:
    the organic intermediate reactant is selected from the group consisting of:
        $(CH_3)_2Si(OH)_2$; $(CH_3)(CF_3CH_2CH_2Si(OH)_2$; $(C_6H_5)(CH_3)Si(OH)_2$; $(CH_3CH_2)_2Ge(OH)_2$; $(CH_3)Si(OH)_3$; 1,3,5,7-tetramethyl-1,3,5,7-tetrahydroxy-cyclotetrasiloxane; 1,3-bis(hydroxy)tetramethyldisiloxane; $[(HO)_2(CH_3)SiO]_3SiCH_3$, 3-glycidoxypropyldimethylsilanol, $HO(CH_2)_4(CH_3)_2SiOH$, trimethylsilanol, or a combination thereof,
    the hydrolase enzyme is selected from the group consisting of *Candida antarctica* lipase, *Candida antarctica* lipase B, *Rhizomucor miehei* lipase, wheat germ lipase, trypsin, cutinase, or a combination thereof; and
    the hydrolase enzyme catalyzes the condensation of the organic intermediate reactant to form the organic molecule.

13. A method of forming an organic molecule, comprising contacting a hydrolase enzyme comprising trypsin, cutinase, or a combination thereof, with an organic reactant selected from the group consisting of: $(CH_3)_2Si(OCH_3)_2$; $(CH_3)(CF_3CH_2CH_2)Si(OCH_3)_2$; $C_6H_5(CH_3)Si(OCH_3)_2$; $(CH_3CH_2)_2Ge(OCH_2CH_3)_2$; $(CH_3)Si(OCH_2CH_3)_3$; 1,3,5,7-tetramethyl-1,3,5,7-tetramethoxy-cyclotetrasiloxane; 1,3-bis(hydroxy)tetramethyldisiloxane; $[(HO)_2(CH_3)SiO]_3SiCH_3$, $(Me_3SiO(CH_2CH_2O)_4CH_3)$, 3-glycidoxypropyldimethylethoxysilane, 1,1-dimethyl-1-sila-2-oxacyclohexane, trimethylsilanol, trimethylethoxysilane or a combination thereof; wherein the hydrolase enzyme catalyzes the hydrolysis and condensation of the organic reactant to form the organic molecule.

* * * * *

UNITED STATES PATENT AND TRADEMARK OFFICE
CERTIFICATE OF CORRECTION

PATENT NO. : 7,455,998 B2
APPLICATION NO. : 10/791951
DATED : November 25, 2008
INVENTOR(S) : Brandstadt et al.

It is certified that error appears in the above-identified patent and that said Letters Patent is hereby corrected as shown below:

Col. 30, line 6 "$(CH_{32}Si(OH)_2$" should read --$(CH_3)_2Si(OH)_2$--

Col. 30, line 6 "$(_6H_5)$" should read --$(C_6H_5)$--

Signed and Sealed this

Seventh Day of April, 2009

JOHN DOLL
*Acting Director of the United States Patent and Trademark Office*